United States Patent
Yang et al.

(10) Patent No.: US 11,673,884 B2
(45) Date of Patent: Jun. 13, 2023

(54) MATRIX METALLOPROTEINASE (MMP) INHIBITORS AND METHODS OF USE THEREOF

(71) Applicant: Foresee Pharmaceuticals Co., Ltd., Taipei (TW)

(72) Inventors: Wenjin Yang, Foster City, CA (US); Kai-Wei Chang, Taichung (TW)

(73) Assignee: Foresee Pharmaceuticals Co., Inc., Taipei (TW)

( * ) Notice: Subject to any disclaimer, the term of this patent is extended or adjusted under 35 U.S.C. 154(b) by 100 days.

(21) Appl. No.: 17/097,314

(22) Filed: Nov. 13, 2020

(65) Prior Publication Data

US 2021/0171509 A1    Jun. 10, 2021

Related U.S. Application Data

(60) Provisional application No. 62/935,358, filed on Nov. 14, 2019.

(51) Int. Cl.
| | |
|---|---|
| *C07D 401/14* | (2006.01) |
| *C07D 405/14* | (2006.01) |
| *C07D 409/14* | (2006.01) |
| *C07D 403/14* | (2006.01) |

(52) U.S. Cl.
CPC ......... *C07D 405/14* (2013.01); *C07D 401/14* (2013.01); *C07D 403/14* (2013.01); *C07D 409/14* (2013.01); *C12Y 304/24065* (2013.01)

(58) Field of Classification Search
CPC ... C07D 401/14; C07D 405/14; C07D 409/14
See application file for complete search history.

(56) References Cited

U.S. PATENT DOCUMENTS

| | | |
|---|---|---|
| 7,179,831 B2 | 2/2007 | Yang |
| 8,153,673 B2 | 4/2012 | Eriksson |
| 2019/0352287 A1 | 11/2019 | Yang |

OTHER PUBLICATIONS

International Search Report dated Feb. 5, 2021 in PCT/US2020/060387.
Written Opinion dated Feb. 5, 2021 in PCT/US2020/060387.
PubChem-CID-137751984, Create Date: Apr. 16, 2019 (Apr. 16, 2019), p. 2, Fig.

*Primary Examiner* — Brian E McDowell
(74) *Attorney, Agent, or Firm* — Ice Miller LLP

(57) ABSTRACT

Hydantoin based compounds of formula (I) useful as inhibitors of matrix metalloproteinases (MMPs), particularly macrophage elastase (MMP-12) are described. Also described are related compositions and methods of using the compounds to inhibit MMP-12 and treat diseases mediated by MMP-12, such as asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

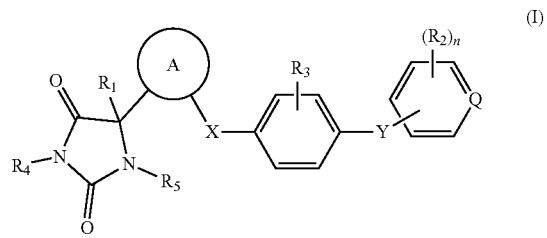

20 Claims, No Drawings

MATRIX METALLOPROTEINASE (MMP) INHIBITORS AND METHODS OF USE THEREOF

CROSS REFERENCE TO RELATED APPLICATION

This application claims priority to U.S. Provisional Patent Application No. 62/935,358, filed Nov. 14, 2019, the disclosure of which is incorporated herein by reference.

BACKGROUND OF THE INVENTION

Matrix metalloproteinases (MMPs) are a superfamily of proteinase enzymes that are important for the degradation of most extracellular matrix proteins during organogenesis, growth, and normal tissue turnover. MMPs are also believed to be important in the uncontrolled breakdown of connective tissue, which relates to a few disease processes such as rheumatoid arthritis, osteoarthritis, gastric ulceration, asthma, emphysema, and tumor metastasis. Therefore, inhibition of one or more MMPs may be of benefit in these diseases.

Human macrophage elastase (MMP-12) is a particular MMP. MMP-12 exhibits all the characteristics of other MMPs, but is preferentially produced from macrophages infiltrating into tissues where injury or remodeling is occurring, and degrades extracellular matrix. For example, increased levels of MMP-12 have been observed during the onset of emphysema. Additionally, an MMP-12 knock-out mouse model showed no development of emphysema after being exposed for a lengthy period of time to cigarette smoke (Hautamkai et al. *Science,* 1997, 277: 2002-2004). These data suggest that MMP-12 plays a role in disease progression of emphysema. The involvement of MMP-12 in the development of chronic asthma has also been suggested based on studies in an MMP-12 deficient model of asthma (Warner et al. *Am J Pathol.* 2004; 165(6): 1921-1930). In the Fas-induced model of acute lung injury, MMP12-deficient mice are protected from developing pulmonary fibrosis (Matute-Bello et al., *Am J Respir Cell Mol Biol.* 2007; 37(2): 210-221). In a model of pulmonary and hepatic fibrosis induced by *Schistosoma mansoni* infection, MMP-12 has profibrotic activities in the lung and liver (Madala et al. *J Immunol* 2010; 184:3955-3963). MMP-12 may also contribute to Idiopathic pulmonary fibrosis (IPF) pathogenesis by cleaving extracellular matrix (ECM) proteins, as BALF levels of a type IV collagen fragment generated by MMP-12 are increased in patients with IPF (Sand et al. *PLoS One* 2013; 8:e84934), and human MMP-12 can cleave a number of human ECM proteins in vitro (Owen et al. *J Leukoc Biol* 1999; 65:137-150). Together, these results suggest that inhibitors of MMP-12 may be useful in the treatment of pulmonary diseases, such as chronic obstructive pulmonary disease (COPD), emphysema, asthma, acute lung injury, idiopathic pulmonary fibrosis (IPF), liver fibrosis and non-alcoholic steatohepatitis (NASH).

MMP-12 has been shown to be secreted from alveolar macrophages of smokers (Shapiro et al., *Journal of Biological Chemistry,* 1993, 268: 23824), in foam cells in atherosclerotic lesions (Matsumoto et al., *Am. J. Pathol.,* 1998, 153: 109), and in a nephritis rat model (Kaneko et al., *J. Immunol.,* 2003, 170:3377). MMP-12 also plays a role in coronary artery disease (Jormsjo et al., *Circulation Research,* 2000, 86: 998). MMP-12 was also shown to be upregulated in inflammatory bowel disease (IBD) patients as well as in a T-cell mediated model of colitis and contribute to epithelial degradation and MMP-12-/- mice were protected against TNBS induced colitis (Pender et al., *Ann N Y Acad Sci.* 2006, 1072:386-8.). Epithelial and stromal MMP-12 along with MMP-3 and -7 have been also upregulated in pouch mucosa of pediatric onset UC, suggesting that the expression of MMPs pediatric UC pouch in the long-term shares characteristics with IBD (Makitalo et al., *World J Gastroenterol.* 2012, 18(30):4028-36). Taken together, these observations suggest that MMP-12 could be a target for treatment of these diseases.

In view of the involvement of MMP-12 in a number of diseases, attempts have been made to prepare inhibitors of MMP-12. A number of MMP-12 inhibitors are known (see e.g., International Patent Application Publication WO 00/40577; European Patent Application Publication EP 1 288 199 A1; U.S. Pat. No. 6,352,9761, and U.S. Patent Application Publication No. 2004/0072871; and European Patent Application Publication EP1394159).

A particular class of MMP inhibitors that have been described are the hydantoin derivatives. For example, International Patent Application Publication WO 02/096426 describes hydantoin derivatives of the general formula:

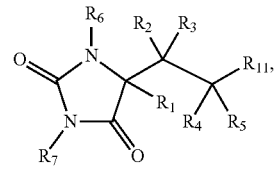

which are disclosed as being active as MMP inhibitors, particularly against tumor necrosis factor-alpha converting enzyme (TACE) and aggrecanase. A feature of the disclosed structures of these derivatives is a spiro-linkage between the hydantoin ring and its side chain. U.S. Patent Application Publication No. 2004/0067996 and International Patent Application Publication WO 2004/108086 describe similar hydantoin derivatives of the general formula:

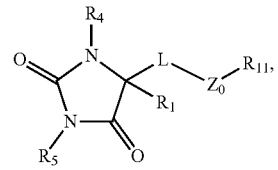

which are also described as MMP inhibitors, particularly for TACE and aggrecanase.

International Patent Application Publication WO 02/074752 describes the synthesis of MMP inhibitors and International Patent Application Publication WO 2004/020415 discloses MMP-12 inhibitors, which are hydantoin derivatives of the general formula:

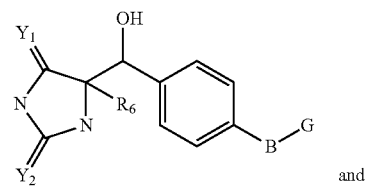

and

-continued

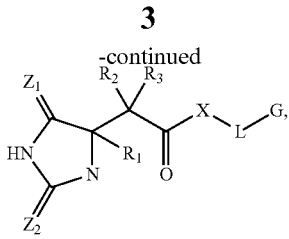

respectively. Some of the disclosed compounds showed MMP inhibitory activities, including MMP-12 inhibitory activity.

More recently, inhibitors of MMP-12 have been described in U.S. Pat. No. 7,179,831, which are hydantoin derivatives of the general formula:

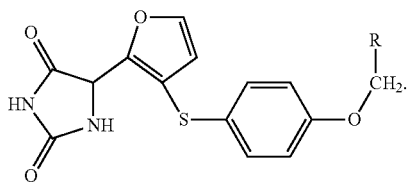

Hydantoin derivatives are a useful class of MMP inhibitors. However, there is a need in the art to identify hydantoin derivatives having improved specificity, potency, and pharmacological properties.

BRIEF SUMMARY OF THE INVENTION

The application satisfies this need by providing hydantoin derivatives having high activity and specificity for MMPs, particularly for macrophage elastase (MMP-12).

In a general aspect, provided is a compound of formula (I):

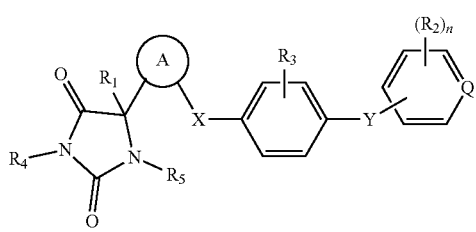

or a tautomer, stereoisomer, pharmaceutically acceptable salt, or solvate thereof,
wherein:
  ring A is an optionally substituted heteroaryl;
  Q is $CR_2$ or N;
  $R_1$ is hydrogen or alkyl;
  each $R_2$ is independently hydrogen, alkyl, halo, hydroxyl, haloalkyl, alkoxy, alkylthio, amino, amido, alkylamino, aminoalkyl, cyano, hydroxyalkyl, —$(CH_2)_pC(O)OR_6$, or —$(CH_2)_pOC(O)R_6$;
  $R_3$ is hydrogen, halo, or alkyl;
  each $R_4$ and $R_5$ is independently hydrogen or alkyl;
  each $R_6$ is independently hydrogen or alkyl, wherein the alkyl is unsubstituted or substituted with one or more groups independently selected from amino, hydroxyl, halo, and alkoxy;
  X is S or O;

Y is:

n is 1, 2, 3 or 4; and
p is 0, 1, 2, 3, 4, or 5.

In an embodiment, provided is a compound of formula (I), or a tautomer, stereoisomer, pharmaceutically acceptable salt, or solvate thereof, wherein ring A is a 5- to 6-membered monocyclic heteroaryl having 1 to 3 heteroatoms independently selected from O, S and N, wherein the 5- to 6-membered monocyclic heteroaryl is optionally substituted with alkyl.

In an embodiment, provided is a compound of formula (I), or a tautomer, stereoisomer, pharmaceutically acceptable salt, or solvate thereof, wherein ring A is pyridinyl, furanyl, thienyl, or N-methyl pyrazolyl.

In an embodiment, provided is a compound of formula (I), or a tautomer, stereoisomer, pharmaceutically acceptable salt, or solvate thereof, wherein ring A is:

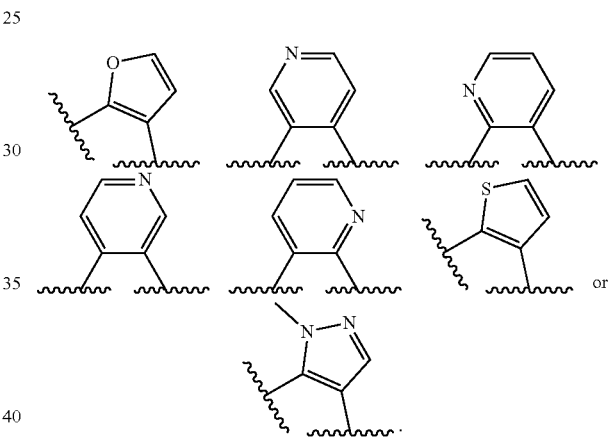

In an embodiment, provided is a compound of formula (I), or a tautomer, stereoisomer, pharmaceutically acceptable salt, or solvate thereof, wherein $R_1$ is hydrogen or $C_{1-4}$.

In an embodiment, provided is a compound of formula (I), or a tautomer, stereoisomer, pharmaceutically acceptable salt, or solvate thereof, wherein $R_2$ is —$CH_3$.

In an embodiment, provided is a compound of formula (I), or a tautomer, stereoisomer, pharmaceutically acceptable salt, or solvate thereof, wherein n is 1 and $R_2$ is —$CH_3$.

In an embodiment, provided is a compound of formula (I), or a tautomer, stereoisomer, pharmaceutically acceptable salt, or solvate thereof, wherein $R_3$ is hydrogen.

In an embodiment, provided is a compound of formula (I), or a tautomer, stereoisomer, pharmaceutically acceptable salt, or solvate thereof, wherein each of $R_4$ and $R_5$ is hydrogen.

In an embodiment, provided is a compound of formula (I), or a tautomer, stereoisomer, pharmaceutically acceptable salt, or solvate thereof, wherein X is S.

In an embodiment, provided is a compound of formula (I), or a tautomer, stereoisomer, pharmaceutically acceptable salt, or solvate thereof, wherein X is O.

In an embodiment, provided is a compound of formula (I), or a tautomer, stereoisomer, pharmaceutically acceptable salt, or solvate thereof, wherein Q is N.

In an embodiment, provided is a compound of formula (I), or a tautomer, stereoisomer, pharmaceutically acceptable salt, or solvate thereof, wherein Y is:

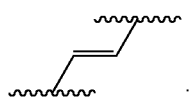

In an embodiment, provided is a compound of formula (I), or a tautomer, stereoisomer, pharmaceutically acceptable salt, or solvate thereof, wherein Y is:

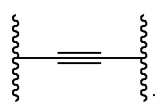

In an embodiment, provided is a compound of formula (I), or a tautomer, stereoisomer, pharmaceutically acceptable salt, or solvate thereof, wherein:

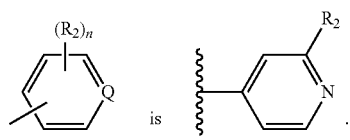

In an embodiment, provided is a compound of formula (I), or a tautomer, stereoisomer, pharmaceutically acceptable salt, or solvate thereof, wherein:

ring A is pyridinyl, furanyl, thienyl, or N-methyl pyrazolyl;

$R_1$ is hydrogen, —$CH_3$ or —$CH_2CH_3$;

$R_2$ is —$CH_3$, —C(O)$NH_2$, —$CH_2OH$, —$OCH_3$, or —OH;

each of $R_3$, $R_4$, and $R_5$ is hydrogen;

X is S or O;

Y is

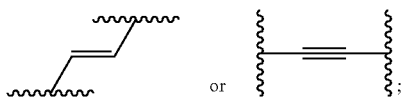

Q is CH or N; and n is 1.

In an embodiment, provided is a compound selected from the group consisting of:

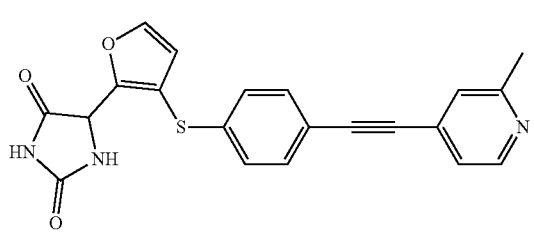

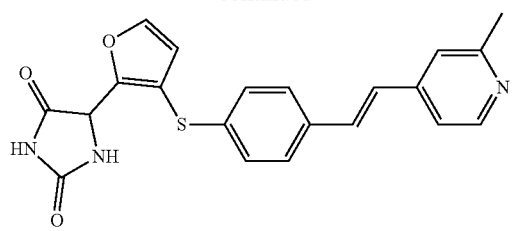

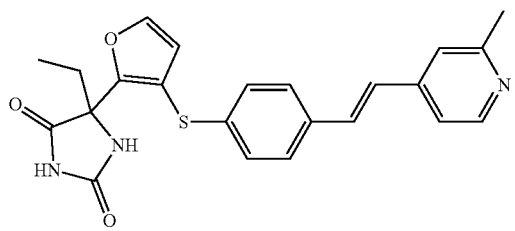

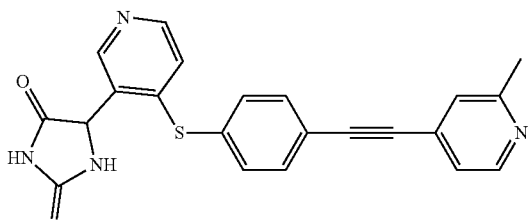

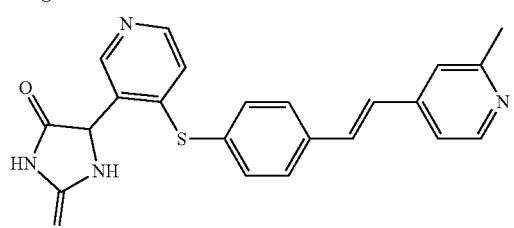

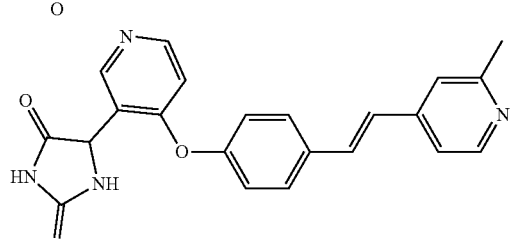

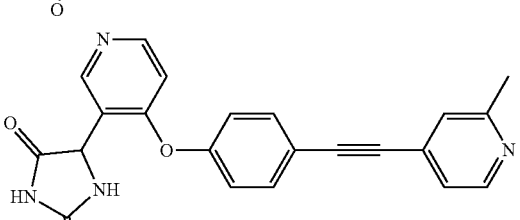

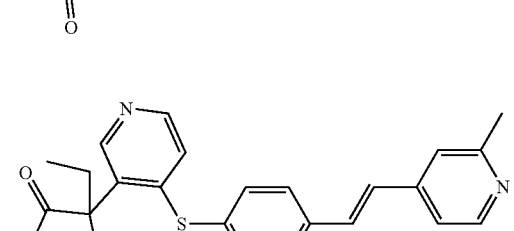

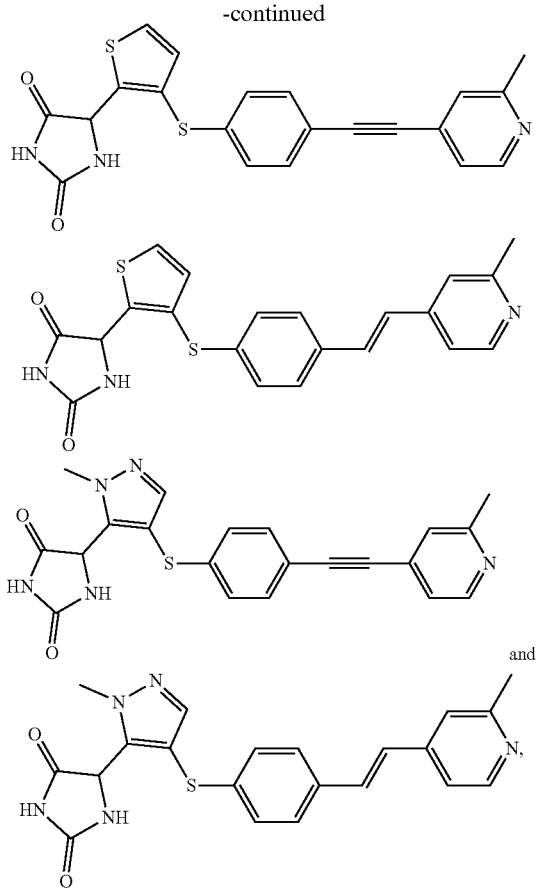

and or a tautomer, stereoisomer, pharmaceutically acceptable salt, or hydrate thereof.

In another general aspect, provided is a pharmaceutical composition comprising a compound of formula as described herein, and at least one pharmaceutically acceptable carrier.

In other general aspects, provided are methods of inhibiting macrophage elastase (MMP-12) in a subject in need thereof, and methods of treating a disease mediated by macrophage elastase (MMP-12) in a subject in need thereof.

In an embodiment, provided is a method of inhibiting macrophage elastase (MMP-12) in a subject in need thereof, comprising administering to the subject a compound or pharmaceutical composition as described herein.

In an embodiment, provided is a method of treating a disease mediated by macrophage elastase (MMP-12) in a subject in need thereof, comprising administering to the subject a compound or pharmaceutical composition as described herein.

In some embodiments, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

Also provided is a compound as described herein, or a tautomer, stereoisomer, pharmaceutically acceptable salt, or solvate thereof, or a composition thereof for use in a method of inhibiting macrophage elastase (MMP-12), or treating a disease mediated by macrophage elastase (MMP-12). In some embodiments, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

Also provided is use of a compound as described herein, or a tautomer, stereoisomer, pharmaceutically acceptable salt, or solvate thereof, or a composition thereof, in the manufacture of a medicament for inhibiting macrophage elastase (MMP-12) or treating a disease mediated by macrophage elastase (MMP-12). In some embodiments, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

In yet another general aspect, provided is a method of preparing a pharmaceutical composition described herein, comprising combining a compound as described herein, or a tautomer, stereoisomer, pharmaceutically acceptable salt, or solvate thereof, and at least one pharmaceutically acceptable carrier.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. For example, the phrase "at least A, B, and C" means that each of A, B, and C is present. The term "at least one of" preceding a series of elements is to be understood to refer to a single element in the series or any combination of two or more elements in the series. For example, the phrase "at least one of A, B, and C" means that only A is present, only B is present, only C is present, both A and B are present, both A and C are present, both B and C are present, or each of A, B, and C is present. Depending on the context, "at least one of" preceding a series of elements can also encompass situations in which any one or more of the elements is present in greater than one instance, e.g., "at least one of A, B, and C" can also encompass situations in which A is present in duplicate alone or further in combination with any one or more of elements B and C.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having."

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Unless otherwise stated, any numerical value, such as a concentration or a concentration range described herein, are to be understood as being modified in all instances by the term "about." Thus, a numerical value typically includes ±10% of the recited value. For example, the recitation of "10-fold" includes 9-fold and 11-fold. As used herein, the use of a numerical range expressly includes all possible subranges, all individual numerical values within that range, including integers within such ranges and fractions of the values unless the context clearly indicates otherwise.

As used herein, "subject" means any animal, preferably a mammal, most preferably a human, to whom will be or has been treated by a method according to an embodiment of the application. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

The phrase "pharmaceutically acceptable salt(s)" means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the application can form pharmaceutically acceptable salts with various amino acids. Suitable base salts include, but are not limited to, aluminum, calcium, lithium, magnesium, potassium, sodium, zinc, bismuth, and diethanolamine salts. For a review on pharmaceutically acceptable salts see Berge et al., 661 Pharm. Sci. 1-19 (1977), incorporated herein by reference.

As used herein, the term "alkyl" means a saturated, monovalent, unbranched or branched hydrocarbon chain. An alkyl group can be unsubstituted or substituted with one or more suitable substituents. Examples of alkyl groups include, but are not limited to, methyl (Me), ethyl (Et), propyl (e.g., n-propyl, isopropyl), butyl (e.g., n-butyl, isobutyl, tert-butyl), and pentyl (e.g., n-pentyl, isopentyl, neopentyl), etc. An alkyl group can have a specified number of carbon atoms. When numbers appear in a subscript after the symbol "C", the subscript defines with more specificity the number of carbon atoms that a particular alkyl can contain. For example, "$C_1$ to $C_{10}$ alkyl" or "$C_{1-10}$ alkyl" is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_4$ alkyl" or "$C_{1-4}$ alkyl" denotes alkyl having one to four carbon atoms.

The term "alkoxy" as used herein refers to an —O-alkyl group, wherein alkyl is as defined above. An alkoxy group is attached to the parent molecule through an oxygen atom. An alkoxy group can have a specified number of carbon atoms. For example, "$C_1$ to $C_{10}$ alkoxy" or "$C_{1-10}$ alkoxy" is intended to include $C_1$, $C_2$, $C_3$, $C_4$, $C_5$, $C_6$, $C_7$, $C_8$, $C_9$, and $C_{10}$ alkoxy groups. Additionally, for example, "$C_1$ to $C_6$ alkoxy" or "$C_{1-6}$ alkoxy" denotes alkoxy having 1 to 6 carbon atoms. Examples of alkoxy include, but are not limited to, methoxy, ethoxy, propoxy (e.g., n-propoxy, isopropoxy), butoxy (e.g., n-butoxy, isobutoxy, tert-butoxy), pentyloxy (e.g., n-pentyloxy, isopentyloxy, neopentyloxy), etc. An alkoxy group can be unsubstituted or substituted with one or more suitable substituents. Similarly, "alkylthio" or "thioalkoxy" represents an alkyl group as defined above attached through a sulfur bridge, for example, —S—methyl, —S-ethyl, etc. Representative examples of alkylthio include, but are not limited to, —$SCH_3$, —$SCH_2CH_3$, etc.

As used herein, the term "halogen" means fluorine, chlorine, bromine, or iodine. Correspondingly, the term "halo" means fluoro (—F), chloro bromo (—Br), and iodo (—I).

"Haloalkyl" is intended to include both branched and straight-chain saturated aliphatic hydrocarbon groups substituted with one or more halogen atoms. Examples of haloalkyl include, but are not limited to, fluoromethyl, difluoromethyl, trifluoromethyl, chloromethyl, dichloromethyl, trichloromethyl, pentafluoroethyl, pentachloroethyl, 2,2,2-trifluoroethyl, heptafluoropropyl, and heptachloropropyl.

The terms "hydroxy" and "hydroxyl" can be used interchangeably, and refer to —OH.

The term "carboxy" refers to —COOH.

The term "cyano" refers to —CN.

The term "amino" refers to —$NH_2$. The term "alkylamino" refers to an amino group in which one or both of the hydrogen atoms attached to nitrogen is substituted with an alkyl group. For example, alkylamino includes methylamino (—$NHCH_3$), dimethylamino (—$N(CH_3)_2$), —$NHCH_2CH_3$, etc.

The term "aminoalkyl" as used herein is intended to include both branched and straight-chain saturated aliphatic hydrocarbon groups substituted with one or more amino groups. For example, "$C_{1-4}$ aminoalkyl" is intended to include $C_1$, $C_2$, $C_3$, and $C_4$ alkyl groups substituted with one or more amino groups. Representative examples of aminoalkyl groups include, but are not limited to, —$CH_2NH_2$, —$CH_2CH_2NH_2$, and —$CH_2CH(NH_2)CH_3$.

As used herein, "amido" refers to —$C(O)N(R)_2$, wherein each R is independently an alkyl group or a hydrogen. Examples of amidos include, but are not limited to, —$C(O)NH_2$, —$C(O)NHCH_3$, and —$C(O)N(CH_3)_2$.

The terms "hydroxylalkyl" and "hydroxyalkyl" are used interchangeably, and refer to an alkyl group substituted with one or more hydroxyl groups. The alkyl can be a branched or straight-chain aliphatic hydrocarbon. Examples of hydroxylalkyl include, but are not limited to, hydroxylmethyl (—$CH_2OH$), hydroxylethyl (—$CH_2CH_2OH$), etc.

The term "aryl" as used herein is a group that contains any carbon-based aromatic group including, but not limited to, phenyl, naphthyl, anthracenyl, phenanthranyl, and the like. Aryl moieties are well known and described, for example, in Lewis, R. J., ed., *Hawley's Condensed Chemical Dictionary*, 13$^{th}$ Edition, John Wiley & Sons, Inc., New York (1997). An aryl group can be substituted or unsubstituted with one or more suitable substituents. An aryl group can be a single ring structure (i.e., monocyclic) or comprise multiple ring structures (i.e., polycyclic, e.g., bicyclic or tricyclic) that are fused ring structures. For example, an aryl group can be a monocyclic aryl group, e.g., phenyl.

As used herein, the term "heteroaryl" includes stable monocyclic and polycyclic aromatic hydrocarbons that contain at least one heteroatom ring member such as sulfur, oxygen, or nitrogen. Heteroaryl can be monocyclic or polycyclic, e.g., bicyclic or tricyclic. Each ring of a heteroaryl group containing a heteroatom can contain one or two oxygen or sulfur atoms and/or from one to four nitrogen atoms provided that the total number of heteroatoms in each ring is four or less and each ring has at least one carbon atom. For bicyclic heteroaryl groups, the fused rings completing the bicyclic group can contain only carbon atoms and can be saturated, partially saturated, or unsaturated. Heteroaryl groups which are polycyclic, e.g., bicyclic or tricyclic must include at least one fully aromatic ring but the other fused ring or rings can be aromatic or non-aromatic. The heteroaryl group can be attached at any available nitrogen or carbon atom of any ring of the heteroaryl group. Preferably, the term "heteroaryl" refers to 5- or 6-membered monocyclic groups and 9- or 10-membered bicyclic groups which have at least one heteroatom (O, S, or N) in at least one of the rings, wherein the heteroatom-containing ring preferably has 1, 2, or 3 heteroatoms, more preferably 1 or 2 heteroatoms, selected from O, S, and/or N. A heteroaryl group can be unsubstituted, or substituted with one or more suitable substituents. The nitrogen heteroatom(s) of a heteroaryl can be substituted or unsubstituted. The nitrogen and sulfur heteroatom(s) of a heteroaryl can optionally be oxidized (i.e., N→O and $S(O)_r$, wherein r is 0, 1 or 2).

Exemplary monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl. Exemplary bicyclic heteroaryl groups include, but are not limited to, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridinyl, furopyridinyl, dihydroisoindolyl, and tetrahydroquinolinyl.

In accordance with convention used in the art:

is used in structural formulas herein to depict the bond that is the point of attachment of the moiety or substituent to the core, backbone, or parent molecule structure.

When a bond to a substituent is shown to cross a bond connecting two atoms in a ring, then such substituent can be bonded to any atom on the ring.

The term "substituted" as used herein with respect to any organic radical (e.g., alkyl, heteroaryl, etc.) means that at least one hydrogen atom is replaced with a non-hydrogen group, provided that all normal valencies are maintained and that the substitution results in a stable compound. When a particular group is "substituted," that group can have one or more substituents, preferably from one to five substituents, more preferably from one to three substituents, most preferably from one to two substituents, independently selected from the list of substituents. The term "independently" when used in reference to substituents, means that when more than one of such substituents is possible, such substituents can be the same or different from each other. Examples of suitable substituents include, but are not limited to, alkyl, halo, alkoxy, amido, alkythio, amine, alkylamine, aminoalkyl, hydroxyalkyl, hydroxyl, carboxyl, etc., such as $C_{1-4}$ alkyl, $C_{1-3}$ alkoxy, —OH, —COOH, —F, —Cl, —$C(O)NHCH_3$, —$C(O)N(CH_3)_2$.

When any variable occurs more than one time in any constituent or formula for a compound, its definition at each occurrence is independent of its definition at every other occurrence. Thus, for example, if a group is shown to be substituted with 0-3 R groups, then said group can be optionally substituted with up to three R groups, and at each occurrence, R is selected independently from the definition of R.

The terms "optional" or "optionally" mean that the event or circumstance described subsequently can, but need not, occur, and such a description includes the situation in which the event or circumstance does or does not occur. For example, "optionally substituted heteroaryl" means that a substituent group can be, but need not be, present, and such a description includes the situation of the heteroaryl group being substituted by a suitable substituent and the heteroaryl group being not substituted by any substituent.

One skilled in the art will recognize that in certain embodiments compounds described herein can have one or more asymmetric carbon atoms in their structure. As used herein, any chemical formulas with bonds shown only as solid lines and not as solid wedged or hashed wedged bonds, or otherwise indicated as having a particular configuration (e.g., R or S) around one or more atoms, contemplates each possible stereoisomer, or mixture of two or more stereoisomers. In other words, if the stereochemistry of a structure is not specified, the structure is intended to encompass all individual stereoisomers and mixtures thereof. Stereoisomers includes enantiomers and diastereomers. Enantiomers are stereoisomers that are non-super-imposable mirror images of each other. A 1:1 mixture of a pair of enantiomers is a racemate or racemic mixture. Diastereomers (or diastereoisomers) are stereoisomers that are not enantiomers, i.e., they are not related as mirror images, and occur when two or more stereoisomers of a compound have different configurations at one or more of the equivalent stereocenters and are not mirror images of each other. Substituent groups (e.g., alkyl, heterocyclyl, etc.) can contain stereocenters in either the R or S configuration.

Thus, included within the scope of the application are the stereochemically pure isomeric forms of the compounds described herein (i.e., a single enantiomer or a single diastereomer) as well as mixtures thereof including their racemates. When a specific stereoisomer is identified, this means that the stereoisomer is substantially free, i.e., associated with less than 50%, preferably less than 20%, more preferably less than 5%, in particular less than 2% and most preferably less than 1% of the other stereoisomers. For example, when a compound is for instance specified as (R), this means that the compound is substantially free of the (S) isomer. Compounds described herein can be used as racemic mixtures, enantiomerically or diastereomerically enriched mixtures, or as enantiomerically or diastereomerically pure individual stereoisomers.

Stereochemically pure isomeric forms can be obtained by techniques known in the art in view of the present disclosure. For example, diastereoisomers can be separated by physical separation methods such as fractional crystallization and chromatographic techniques, and enantiomers can be separated from each other by the selective crystallization of the diastereomeric salts with optically active acids or bases or by chiral chromatography. Pure stereoisomers can also be prepared synthetically from appropriate stereochemically pure starting materials, or by using stereoselective reactions.

Compounds described herein can also form tautomers. The term "tautomer" refers to compounds that are interchangeable forms of a particular compound structure and that vary in the displacement of hydrogen atoms and electrons. Tautomers are constitutional isomers of chemical compounds that readily interconvert, usually resulting in relocation of a proton (hydrogen). Thus, two structures can be in equilibrium through the movement of pi electrons and an atom (usually hydrogen). All tautomeric forms and mixtures of tautomers of the compounds described herein are included with the scope of the application.

Compounds described herein can exist in solvated and unsolvated forms. The term "solvate" means a physical association, e.g., by hydrogen bonding, of a compound of the application with one or more solvent molecules. The solvent molecules in the solvate can be present in a regular arrangement and/or a non-ordered arrangement. The solvate can comprise either a stoichiometric or nonstoichiometric amount of the solvent molecules. "Solvate" encompasses both solution-phase and isolable solvates. Compounds described herein can form solvates with water (i.e., hydrates) or common organic solvents. Exemplary solvates include, but are not limited to, hydrates, ethanolates, methanolates, and isopropanolates. Methods of solvation are generally known in the art.

Also included within the scope of the application are all isotopes of atoms occurring in the compounds of the application. Isotopes include those atoms having the same atomic number but different mass numbers. By way of general example and without limitation, isotopes of hydrogen include deuterium ($^2$H) and tritium ($^3$H). Isotopes of carbon include $^{13}$C and $^{14}$C. Isotopically-labeled compounds can generally be prepared by conventional techniques known to those skilled in the art or by processes analogous to those described herein, using an appropriate isotopically-labeled reagent in place of the non-labeled reagent otherwise employed.

As used herein, the name of a compound is intended to encompass all possible existing isomeric forms (e.g., enantiomers, diastereomers, racemate or racemic mixture, or any mixture thereof), and tautomers of the compound.

Compounds

In a general aspect, provided herein is a compound of formula (I):

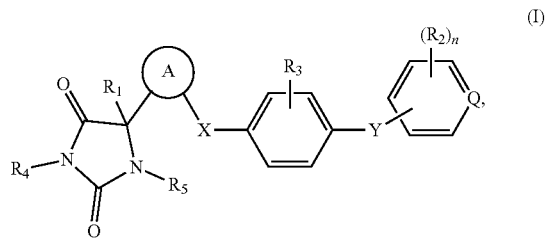

or a tautomer, stereoisomer, pharmaceutically acceptable salt, or solvate thereof,
wherein:
  ring A is an optionally substituted heteroaryl;
  Q is $CR_2$ or N;
  $R_1$ is hydrogen or alkyl;
  each $R_2$ is independently hydrogen, alkyl, halo, hydroxyl, haloalkyl, alkoxy, alkylthio, amino, amido, alkylamino, aminoalkyl, cyano, hydroxyalkyl, —$(CH_2)_pC(O)OR_6$, or —$(CH_2)_pOC(O)R_6$;
  $R_3$ is hydrogen, halo, or alkyl;
  each $R_4$ and $R_5$ is independently hydrogen or alkyl;
  each $R_6$ is independently hydrogen or alkyl, wherein the alkyl is unsubstituted or substituted with one or more groups independently selected from amine, hydroxyl, halo, and alkoxy;
  X is S or O;
  Y is:

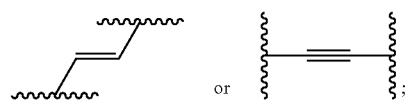

n is 1, 2, 3 or 4; and
  p is 0, 1, 2, 3, 4, or 5.

In an embodiment, provided is a compound of formula (I), or a tautomer, stereoisomer, pharmaceutically acceptable salt, or solvate thereof, wherein Q is N.

In an embodiment, provided is a compound of formula (I), or a tautomer, stereoisomer, pharmaceutically acceptable salt, or solvate thereof, wherein Q is $CR_2$.

In an embodiment, provided is a compound of formula (I), or a tautomer, stereoisomer, pharmaceutically acceptable salt, or solvate thereof, wherein $R_2$ of the moiety

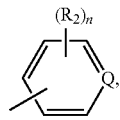

if present, can be attached at any position of the ring. Preferably, n is 1, such that there is one $R_2$ substituent. In other preferred embodiments, the $R_2$ group is attached at the meta position of the ring relative to the bond to variable Y.

In an embodiment, provided is a compound of formula (I), or a tautomer, stereoisomer, pharmaceutically acceptable salt, or solvate thereof, wherein n is 1 and $R_2$ is $C_{1-3}$ alkoxy (e.g., —$OCH_3$, —$OCH_2CH_2CH_3$, —$OCH_2CH_3$, —OCH$(CH_3)_2$), $C_{1-4}$ alkyl (e.g., —$CH_3$, —$CH_2CH_3$, —$CH_2CH(CH_3)_2$), —$CH_2OH$, —OH, —COOH, —$C(O)NH_2$, —$C(O)NHCH_3$, or —$CH_2OC(O)CH(NH_2)CH(CH_3)_2$, —$C(O)NH_2$, or —$C(O)NHCH_3$. Preferably $R_2$ is —$CH_3$, —$C(O)NH_2$, —$CH_2OH$, —$OCH_3$, or OH.

In an embodiment, provided is a compound of formula (I), or a tautomer, stereoisomer, pharmaceutically acceptable salt, or solvate thereof, wherein $R_2$ is —$CH_3$, —$C(O)NH_2$, —$CH_2OH$, —$OCH_3$, or —OH.

In an embodiment, provided is a compound of formula (I), or a tautomer, stereoisomer, pharmaceutically acceptable salt, or solvate thereof, wherein $R_2$ is —$CH_3$.

In an embodiment, provided is a compound of formula (I), or a tautomer, stereoisomer, pharmaceutically acceptable salt, or solvate thereof, wherein $R_3$ is hydrogen.

In an embodiment, provided is a compound of formula (I), or a tautomer, stereoisomer, pharmaceutically acceptable salt, or solvate thereof, wherein:

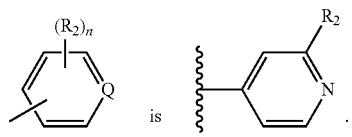

is

In an embodiment, provided is a compound of formula (I), or a tautomer, stereoisomer, pharmaceutically acceptable salt, or solvate thereof, wherein:

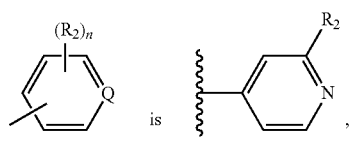

is , wherein $R_2$ is —$CH_3$, —$C(O)NH_2$, —$CH_2OH$, —$OCH_3$, or —OH, and is preferably —$CH_3$.

In an embodiment, provided is a compound of formula (I), or a tautomer, stereoisomer, pharmaceutically acceptable salt, or solvate thereof, wherein

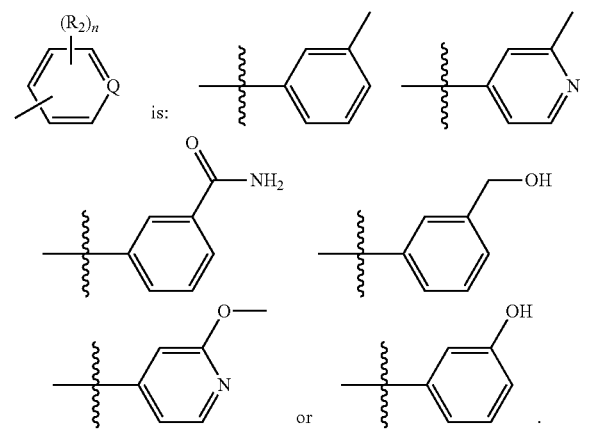

According to embodiments of the application, the chiral carbon atom of the hydantoin moiety can be unsubstituted (i.e., $R_1$ is hydrogen) or substituted. When substituted, the $R_1$ substituent is preferably alkyl. Preferred alkyl groups for substitution of the chiral carbon atom of the hydantoin moiety include $C_{1-4}$ alkyl groups, preferably $C_{1-2}$ alkyl groups, such as methyl and ethyl.

In an embodiment, provided is a compound of formula (I), or a tautomer, stereoisomer, pharmaceutically acceptable salt, or solvate thereof, wherein $R_1$ is hydrogen.

In an embodiment, provided is a compound of formula (I), or a tautomer, stereoisomer, pharmaceutically acceptable salt, or solvate thereof, wherein $R_1$ is $C_{1-4}$ alkyl.

In an embodiment, provided is a compound of formula (I), or a tautomer, stereoisomer, pharmaceutically acceptable salt, or solvate thereof, wherein $R_1$ is —$CH_3$ or —$CH_2CH_3$.

In an embodiment, provided is a compound of formula (I), or a tautomer, stereoisomer, pharmaceutically acceptable salt, or solvate thereof, wherein $R_4$ is hydrogen or —$CH_3$ and $R_5$ is —$CH_3$.

In an embodiment, provided is a compound of formula (I), or a tautomer, stereoisomer, pharmaceutically acceptable salt, or solvate thereof, wherein each of $R_4$ and $R_5$ is hydrogen.

According to embodiments of the application, X is S or O.

In an embodiment, provided is a compound of formula (I), or a tautomer, stereoisomer, pharmaceutically acceptable salt, or solvate thereof, wherein X is O.

In an embodiment, provided is a compound of formula (I), or a tautomer, stereoisomer, pharmaceutically acceptable salt, or solvate thereof, wherein X is S.

In an embodiment, provided is a compound of formula (I), or a tautomer, stereoisomer, pharmaceutically acceptable salt, or solvate thereof, wherein Y is:

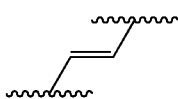

In an embodiment, provided is a compound of formula (I), or a tautomer, stereoisomer, pharmaceutically acceptable salt, or solvate thereof, wherein Y is:

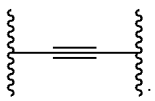 [SMILES: *C#C*]

In an embodiment, provided is a compound of formula (I), or a tautomer, stereoisomer, pharmaceutically acceptable salt, or solvate thereof, wherein n is 1.

In an embodiment, provided is a compound of formula (I), or a tautomer, stereoisomer, pharmaceutically acceptable salt, or solvate thereof, wherein ring A is pyridinyl N-oxide.

In an embodiment, provided is a compound of formula (I), or a tautomer, stereoisomer, pharmaceutically acceptable salt, or solvate thereof, wherein ring A is a 5- to 6-membered monocyclic heteroaryl having 1 to 3 heteroatoms independently selected from O, S, and N, wherein the 5- to 6-membered monocyclic heteroaryl is optionally substituted with alkyl, preferably optionally substituted with methyl. Preferably, ring A is an optionally substituted 5- or 6-membered heteroaryl having 1-2 heteroatoms selected from N, S, and O. In particular embodiments, ring A is a 5-membered heteroaryl ring, such as furanyl, imidazolyl, thienyl, oxazolyl, or pyrazolyl. In other particular embodiments, ring A is a 6-membered heteroaryl, such as pyridinyl or pyridinyl N-oxide. Any positional or regioisomer of the heteroaryl ring can be used, meaning that the hydantoin moiety and X linker can be connected to the heteroaryl at any substitutable carbon atom on the heteroaryl ring. For example, when ring A is a 5-membered heteroaryl ring containing 1 heteroatom, the hydantoin moiety and X linker can be connected to the 5-membered heteroaryl ring in a 2, 3-substitution pattern, a 2, 4-substitution pattern, a 2, 5-substitution pattern, a 3, 4-substitution pattern, etc., relative to the heteroatom. As another illustrative example, when ring A is a 6-membered heteroaryl ring containing one heteroatom, the hydantoin moiety and X linker can be connected to the 6-membered heteroaryl ring in a 2, 3-substitution pattern, a 2, 4-substitution pattern, a 2, 5-substitution pattern, a 2, 6-substitution pattern, a 3, 4-substitution pattern, etc., relative to the heteroatom.

In some embodiments, provided is a compound of formula (I), or a tautomer, stereoisomer, pharmaceutically acceptable salt, or solvate thereof, wherein ring A is substituted. Ring A can be substituted on any substitutable carbon atom of an aryl or heteroaryl ring, or any substitutable heteroatom, e.g., nitrogen atom, of a heteroaryl ring. For example, ring A can be substituted with an alkyl group, e.g., methyl, including substitution with a methyl group for instance on a nitrogen atom of a heteroaryl ring, e.g., imidazolyl or pyrazolyl.

In an embodiment, provided is a compound of formula (I), or a tautomer, stereoisomer, pharmaceutically acceptable salt, or solvate thereof, wherein ring A is a 5- to 6-membered monocyclic heteroaryl having 1 to 2 heteroatoms independently selected from O, S, and N, wherein the 5- to 6-membered monocyclic heteroaryl is optionally substituted with alkyl, preferably optionally substituted with methyl.

In an embodiment, provided is a compound of formula (I), or a tautomer, stereoisomer, pharmaceutically acceptable salt, or solvate thereof, wherein ring A is a 5- to 6-membered monocyclic heteroaryl having 1 heteroatom selected from O, S, and N, wherein the 5- to 6-membered monocyclic heteroaryl is optionally substituted with alkyl, preferably optionally substituted with methyl.

In an embodiment, provided is a compound of formula (I), or a tautomer, stereoisomer, pharmaceutically acceptable salt, or solvate thereof, wherein ring A is pyridinyl.

In an embodiment, provided is a compound of formula (I), or a tautomer, stereoisomer, pharmaceutically acceptable salt, or solvate thereof, wherein ring A is furanyl.

In an embodiment, provided is a compound of formula (I), or a tautomer, stereoisomer, pharmaceutically acceptable salt, or solvate thereof, wherein ring A is thienyl.

In an embodiment, provided is a compound of formula (I), or a tautomer, stereoisomer, pharmaceutically acceptable salt, or solvate thereof, wherein ring A is pyrazolyl optionally substituted with methyl.

In an embodiment, provided is a compound of formula (I), or a tautomer, stereoisomer, pharmaceutically acceptable salt, or solvate thereof, wherein ring A is N-methyl pyrazolyl.

In an embodiment, provided is a compound of formula (I), or a tautomer, stereoisomer, pharmaceutically acceptable salt, or solvate thereof, wherein ring A is:

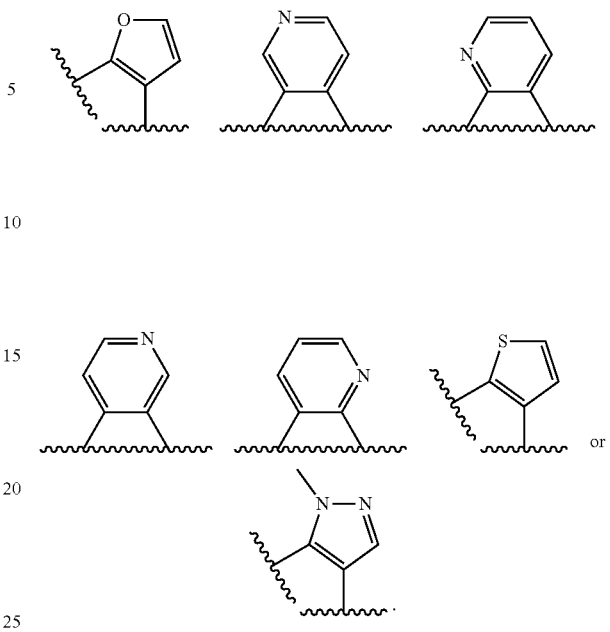

In some embodiments, wherein ring A is furanyl, provided is a compound of formula (II):

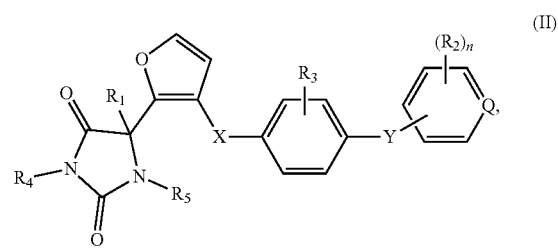

or a tautomer, stereoisomer, pharmaceutically acceptable salt, or solvate thereof, wherein each of the variables are as defined above for the compound of formula (I).

In some embodiments, wherein ring A is pyridinyl, provided is a compound of formula (III):

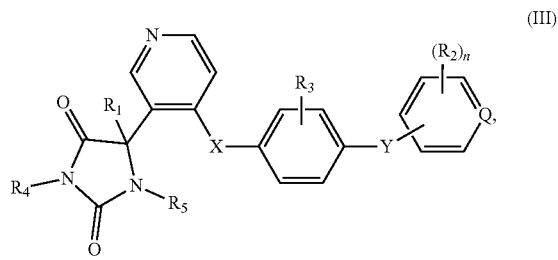

or a tautomer, stereoisomer, pharmaceutically acceptable salt, or solvate thereof, wherein each of the variables are as defined above for the compound of formula (I).

In some embodiments, wherein ring A is thienyl, provided is a compound of formula (IV):

(IV)

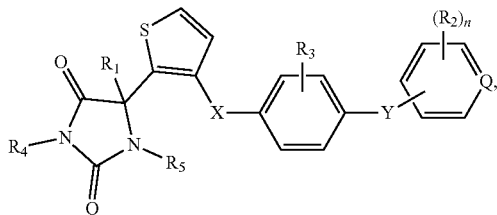

or a tautomer, stereoisomer, pharmaceutically acceptable salt, or solvate thereof, wherein each of the variables are as defined above for the compound of formula (I).

In some embodiments, wherein ring A is N-methyl pyrazolyl, provided is a compound of formula (V):

(V)

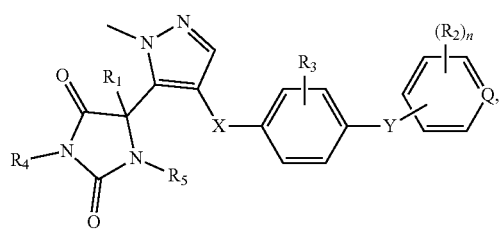

or a tautomer, stereoisomer, pharmaceutically acceptable salt, or solvate thereof, wherein each of the variables are as defined above for the compound of formula (I).

In certain embodiments, provided is a compound of formula (I), or a tautomer, stereoisomer, pharmaceutically acceptable salt, or solvate thereof, wherein:

ring A is pyridinyl;
$R_1$ is hydrogen, —$CH_3$ or —$CH_2CH_3$;
$R_2$ is —$CH_3$, —$C(O)NH_2$, —$CH_2OH$, —$OCH_3$, or —OH;
each of $R_3$, $R_4$, and $R_5$ is hydrogen;
X is S or O;
Y is

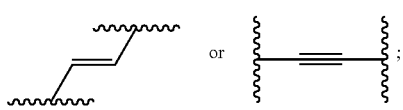

Q is CH or N; and
n is 1.

In certain embodiments, provided is a compound of formula (I), or a tautomer, stereoisomer, pharmaceutically acceptable salt, or solvate thereof, wherein:

ring A is furanyl;
$R_1$ is hydrogen, —$CH_3$ or —$CH_2CH_3$;
$R_2$ is —$CH_3$, —$C(O)NH_2$, —$CH_2OH$, —$OCH_3$, or —OH;
each of $R_3$, $R_4$, and $R_5$ is hydrogen;
X is S or O;
Y is

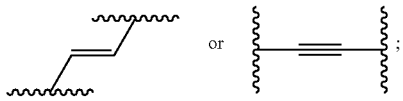

Q is CH or N; and
n is 1.

In certain embodiments, provided is a compound of formula (I), or a tautomer, stereoisomer, pharmaceutically acceptable salt, or solvate thereof, wherein:

ring A is thienyl;
$R_1$ is hydrogen, —$CH_3$ or —$CH_2CH_3$;
$R_2$ is —$CH_3$, —$C(O)NH_2$, —$CH_2OH$, —$OCH_3$, or —OH;
each of $R_3$, $R_4$, and $R_5$ is hydrogen;
X is S or O;
Y is

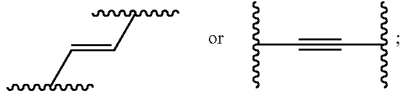

Q is CH or N; and
n is 1.

In certain embodiments, provided is a compound of formula (I), or a tautomer, stereoisomer, pharmaceutically acceptable salt, or solvate thereof, wherein:

ring A is N-methyl pyrazolyl;
$R_1$ is hydrogen, —$CH_3$ or —$CH_2CH_3$;
$R_2$ is —$CH_3$, —$C(O)NH_2$, —$CH_2OH$, —$OCH_3$, or —OH;
each of $R_3$, $R_4$, and $R_5$ is hydrogen;
X is S or O;
Y is

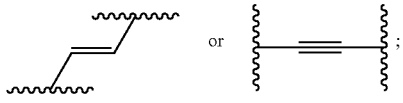

Q is CH or N; and
n is 1.

Exemplary compounds of the application include, but are not limited to, compounds listed in Table 1 below, and any tautomer, stereoisomer, pharmaceutically acceptable salt or solvate thereof. The MMP-12 $IC_{50}$ values were determined according to the assay described in Example 1 below. The $IC_{50}$ values are reported as follows: A=less than 1 nM, B=1 nM to 10 nM, C=10 nM to 100 nM, D=greater than 100 nM.

TABLE 1

Exemplary Compounds of the Application

| Compound ID | Structure | Analytical Data (LCMS, NMR, etc.) | MMP-12 IC$_{50}$ (nM) |
| --- | --- | --- | --- |
| AC-1 | 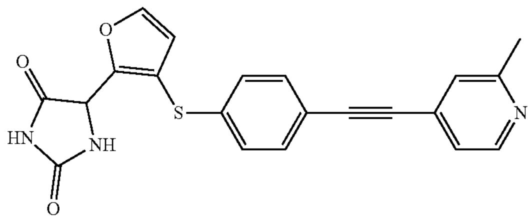 [SMILES: Cc1cc(C#Cc2ccc(Sc3ccoc3C3NC(=O)NC3=O)cc2)ccn1] | 1H NMR (400 MHz, CD3OD) δ: 8.20 (d, J = 4.0 Hz, 1H), 7.66-7.57 (m, 5H), 7.01 (s, 1H), 6.93 (d, J = 4.0 Hz, 1H), 6.64 (s, 1H), 5.49 (s, 1H), 2.44 (s, 3H); m/z (ESI+) (M + H)+ = 390.15, (M − H)− = 388.20; HPLC tR = 5.035 min. | C |
| AC-2 | 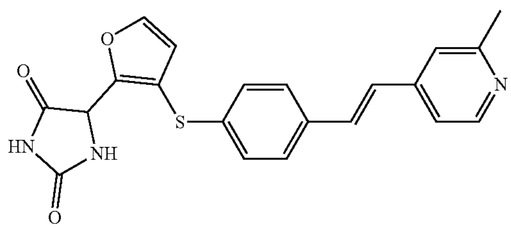 [SMILES: Cc1cc(/C=C/c2ccc(Sc3ccoc3C3NC(=O)NC3=O)cc2)ccn1] | 1H NMR (400 MHz, CD3OD) δ: 8.313 (d, J = 5.2 Hz, 1H), 7.671 (d, J = 2.0 Hz, 1H), 7.525 (d, J = 8.4 Hz, 2H), 7.384-7.356 (m, 3H), 7.233 (d, J = 8.4 Hz, 2H), 7.113 (d, J = 16.4 Hz, 1H), 6.491 (d, J = 2.0 Hz, 1H), 5.492 (s, 1H), 2.512 (s, 3H); m/z (ESI+) (M + H)+ = 392.10, (M − H)− = 390.05; HPLC tR = 4.796 min. | A |
| AC-3 | 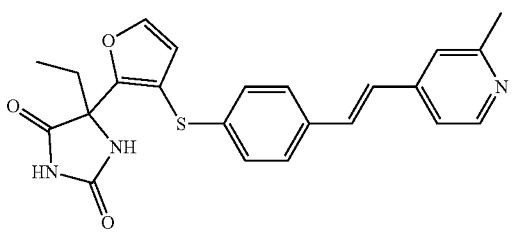 [SMILES: CCC1(c2occc2Sc2ccc(/C=C/c3ccnc(C)c3)cc2)NC(=O)NC1=O] | 1H-NMR (400 MHz DMSO) δ: 10.948 (s, 1H), 8.439 (s, 1H), 8.369 (d, J = 5.2 Hz, 1H), 7.840 (d, J = 2.0 Hz, 1H), 7.550 (d, J = 8.4 Hz, 2H), 7.466-7.373 (m, 3H), 7.309 (d, J = 4.8 Hz, 1H), 7.164-7.127 (m, 3H), 6.517 (d, J = 2.0 Hz, 1H), 2.432 (s, 3H), 2.190-2.126 (m, 2H), 0.856-0.819 (m, 3H); m/z (ESI+) (M + H)+ = 420.20, (M − H)− = 418.10; HPLC tR = 5.021 min. | A |
| AC-4 | 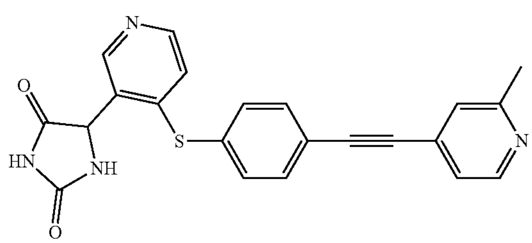 [SMILES: Cc1cc(C#Cc2ccc(Sc3ccncc3C3NC(=O)NC3=O)cc2)ccn1] | 1H NMR (400 MHz, CD3OD) δ: 8.432 (s, 1H), 8.418 (d, J = 5.2 Hz, 1H), 8.301 (d, J = 5.6 Hz, 1H), 7.650 (d, J = 8.4 Hz, 2H), 7.555 (d, J = 8.0 Hz, 2H), 7.417 (s, 1H), 7.330 (d, J = 4.8 Hz, 1H), 7.003 (d, J = 5.6 Hz, 1H), 5.613 (s, 1H), 2.531 (s, 3H); m/z (ESI+) (M + H)+ = 401.10; HPLC tR = 4.598 min. | B |
| AC-5 | 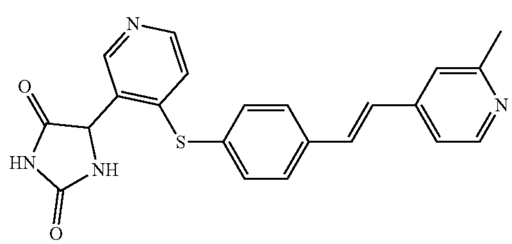 [SMILES: Cc1cc(/C=C/c2ccc(Sc3ccncc3C3NC(=O)NC3=O)cc2)ccn1] | 1H-NMR (400 MHz DMSO) δ: 10.998 (s, 1H), 8.413-8.403 (m, 3H), 8.321 (d, J = 5.2 Hz, 1H), 7.738 (d, J = 8.0 Hz, 2H), 7.516 (s, 1H), 7.493-7.473 (m, 3H), 7.417 (s, 1H), 7.353 (d, J = 5.6 Hz, 1H), 7.298 (s, 1H), 7.257 (s, 1H), 6.844 (d, J = 5.6 Hz, 1H), 5.513 (s, 1H), 2.464 (s, 3H); m/z (ESI+) (M + H)+ = 403.20, (M − H)− = 401.25; HPLC tR = 3.779 min. | A |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| AC-6 | 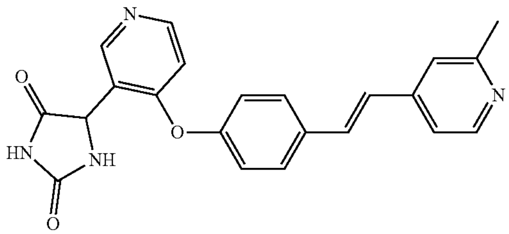 | 1H NMR (400 MHz, CD3OD) δ: 8.492 (s, 1H), 8.413 (d, J = 5.2 Hz, 1H), 8.336 (d, J = 5.2 Hz, 1H), 7.729 (d, J = 8.4 Hz, 2H), 7.505-7.381 (m, 4H), 7.159-7.118 (m, 3H), 6.817 (d, J = 6.0 Hz, 1H), 5.416 (s, 1H), 2.525 (s, 3H); m/z (ESI+) (M + H)+ = 387.20; HPLC tR = 3.425 min. | A |
| AC-7 | 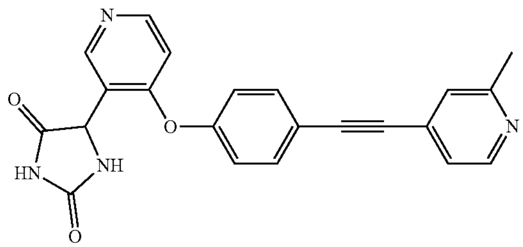 [SMILES: Cc1cc(C#Cc2ccc(Oc3ccncc3C3NC(=O)NC3=O)cc2)ccn1] | 1H NMR (400 MHz, CD3OD) δ: 8.514 (s, 1H), 8.441-8.393 (m, 2H), 7.667 (d, J = 7.2 Hz, 2H), 7.402 (s, 1H), 7.316 (d, J = 5.2 Hz, 1H), 7.179 (d, J = 6.8 Hz, 2H), 6.849 (d, J = 5.6 Hz, 1H), 5.423 (s, 1H), 2.527 (s, 3H); m/z (ESI+) (M + H)+ = 385.15; HPLC tR = 5.652 min. | B |
| AC-8 | 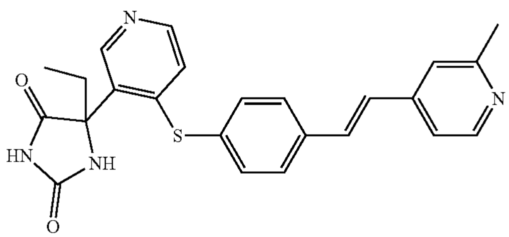 [SMILES: CCC1(c2cnccc2Sc2ccc(/C=C/c3ccnc(C)c3)cc2)NC(=O)NC1=O] | 1H NMR (400 MHz, CDCl3) δ: 8.641 (s, 1H), 8.476 (d, J = 5.6 Hz, 1H), 8.205 (d, J = 5.2 Hz, 1H), 7.581 (d, J = 8.4 Hz, 2H), 7.454-7.375 (m, 5H), 7.087 (d, J = 16.4 Hz, 1H), 6.845 (d, J = 5.6 Hz, 1H), 2.695 (s, 3H), 2.417-2.305 (m, 2H), 1.038 (t, J = 7.6 Hz, 3H); m/z (ESI+) (M + H)+ = 431.35, (M − H)− = 429.25; HPLC tR = 6.062 min. | A |
| AC-9 | 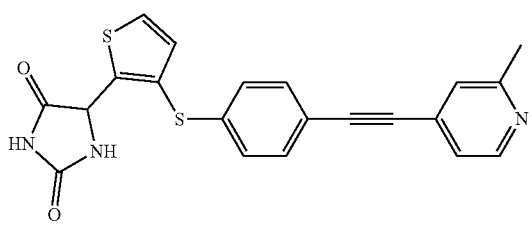 | 1H NMR (400 MHz, MeOD) δ: 8.389 (d, J = 5.2 Hz, 1H), 7.603 (d, J = 5.2 Hz, 1H), 7.444 (d, J = 8.4 Hz, 2H), 7.375 (s, 1H), 7.277 (d, J = 5.2 Hz, 1H), 7.191 (d, J = 8.4 Hz, 2H), 7.044 (d, J = 5.2 Hz, 1H), 5.719 (s, 1H), 2.519 (s, 3H); m/z (ESI+) (M + H)+ = 406.15, (M − H)− = 404.05; HPLC tR = 5.671 min | A |
| AC-10 | 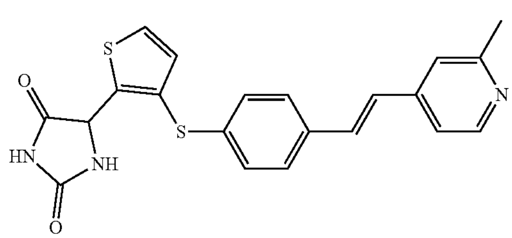 | 1H NMR (400 MHz, DMSO-d6) δ: 10.956 (s, 1H), 8.570 (s, 1H), 8.410 (d, J = 5.2 Hz, 1H), 7.729 (d, J = 5.6 Hz, 1H), 7.600 (d, J = 8.4 Hz, 2H), 7.503 (d, J = 16.4 Hz, 1H), 7.411 (s, 1H), 7.347 (d, J = 5.2 Hz, 1H), 7.227 (d, J = 8.4 Hz, 2H), 7.202 (d, J = 16.4 Hz, 1H), 7.050 (d, J = 5.2 Hz, 1H), 5.662 (s, 1H), 2.474 (s, 3H); m/z (ESI+) (M + H)+ = 408.20, (M − H)− = 406.15; HPLC tR = 5.657 min. | A |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| AC-11 | 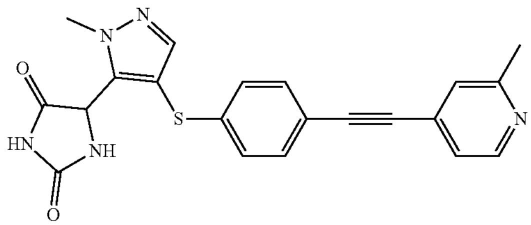 [SMILES: Cc1cc(C#Cc2ccc(Sc3cnn(C)c3C3NC(=O)NC3=O)cc2)ccn1] | 1H NMR (400 MHz, DMSO-d6) δ: 11.013 (s, 1H), 8.442 (d, J = 5.2 Hz, 1H), 8.255 (s, 1H), 7.660 (s, 1H), 7.434 (d, J = 8.4 Hz, 2H), 7.348 (s, 1H), 7.260 (d, J = 5.2 Hz, 1H), 7.065 (d, J = 8.4 Hz, 2H), 5.603 (s, 1H), 3.847 (s, 3H), 2.437 (s, 3H); m/z (ESI+) (M + H)+ = 404.20, (M − H)− = 402.05; HPLC tR = 5.182 min. | A |
| AC-12 | 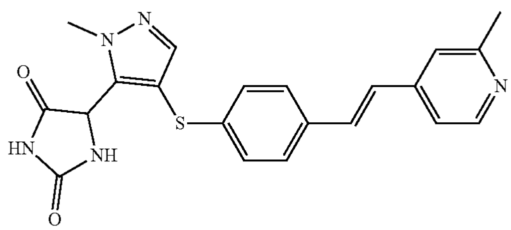 [SMILES: Cc1cc(/C=C/c2ccc(Sc3cnn(C)c3C3NC(=O)NC3=O)cc2)ccn1] | 1H NMR (400 MHz, DMSO-d6) δ: 11.038 (s, 1H), 8.360 (d, J = 5.2 Hz, 1H), 8.271 (s, 1H), 7.631 (s, 1H), 7.499 (d, J = 8.4 Hz, 2H), 7.444 (d, J = 16.4 Hz, 1H), 7.364 (s, 1H), 7.299 (d, J = 5.2 Hz, 1H), 7.130 (d, J= 16.8 Hz, 1H), 7.067 (d, J = 8.4 Hz, 2H), 5.605 (s, 1H), 3.832 (s, 3H), 2.428 (s, 3H); m/z (ESI+) (M + H)+ = 406.25, (M − H)− = 404.20; HPLC tR = 5.260 min. | A |

Compounds of the application can be prepared by any number of processes as described generally below and more specifically illustrated by the exemplary examples, which follow herein. The compounds provided herein as prepared in the processes described below can be synthesized in the form of mixtures of stereoisomers (e.g., enantiomers, diastereomers), including racemic mixtures of enantiomers, that can be separated from one another using art-known resolution procedures, for instance including liquid chromatography using a chiral stationary phase. Additionally or alternatively, stereochemically pure isomeric forms of the compounds described herein can be derived from the corresponding stereochemically pure isomeric forms of the appropriate starting materials, intermediates, or reagents. For example, if a specific stereoisomer is desired, the compound can be synthesized by stereospecific methods of preparation, which typically employ stereochemically pure starting materials or intermediate compounds.

By way of illustration, but not as a limitation, embodiments of compounds of formula (I), wherein Y is can be prepared according any one of General Schemes 1-3; and embodiments of compounds of formula (II), wherein Y is

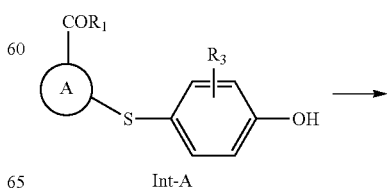
, can be prepared according to any one of General Schemes 4-6. One of ordinary skill in the art will recognize that, to obtain various compounds of formula (I) as described herein, starting materials can be suitably selected so that the ultimately desired substituent groups will be carried through (i.e., be stable over the course of the synthesis) the reaction scheme with or without protection as appropriate to yield the desired product. Alternatively, it may be necessary or desirable to employ, in place of the ultimately desired substituent, a suitable group that may be carried through (i.e., be stable over the course of the synthesis) the reaction scheme and replaced as appropriate with the desired substituent.

General Scheme 1[1]

Int-A

27
-continued

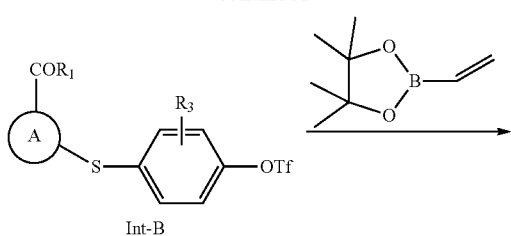
Int-B

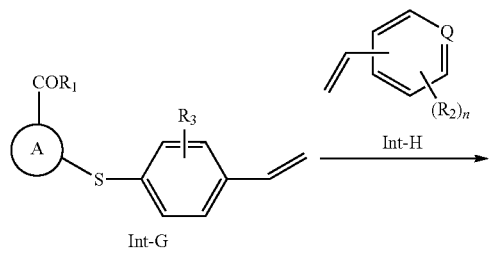
Int-G

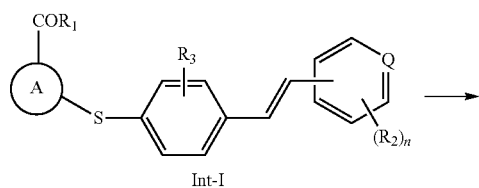
Int-I

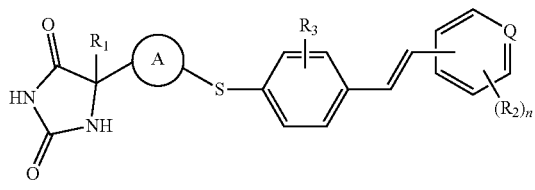
(I)

[1]X is halo and the remaining variable group are as defined herein for the compounds of formula (I)

(CF$_3$SO$_2$)$_2$O is added to a solution of Int-A in an organic solvent to obtain Int-B. Then, 4,4,5,5-tetramethyl-2-vinyl-1,3,2-dioxaborolane and palladium catalyst are added to a solution of Int-B. After completion of the reaction, the mixture is extracted to obtain Int-G. To a solution of Int-G, Int-H and a catalyst are added to obtain Int-I. Then, Int-I is reacted with (NH$_4$)$_2$CO$_3$ and potassium cyanide (KCN) in aqueous alcohol to obtain embodiments of the compounds of formula (I) described herein.

General Scheme 2[1]

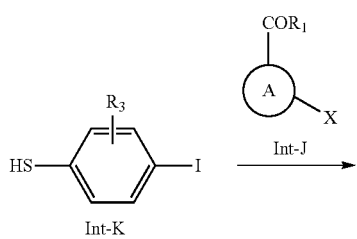
Int-K

28
-continued

Int-L

Int-I (I)

[1]X is halo and the remaining variable group are defined herein for the compounds of formula (I)

To a solution of Int-K in organic solvent, Int-J and K$_2$CO$_3$ are added and the mixture is stirred. The reaction mixture is extracted to obtain Int-L. Int-H and a palladium catalyst are added to a solution of Int-L and the reaction mixture is stirred followed by extraction to obtain Int-I. Then, Int-I is reacted with (NH$_4$)$_2$CO$_3$ and potassium cyanide (KCN) in aqueous alcohol as described above for General Scheme 2 to obtain embodiments of the compounds of formula (I) described herein.

General Scheme 3[1]

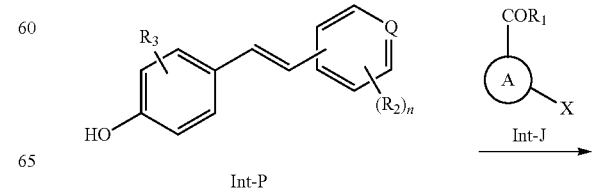
Int-O

Int-P

-continued

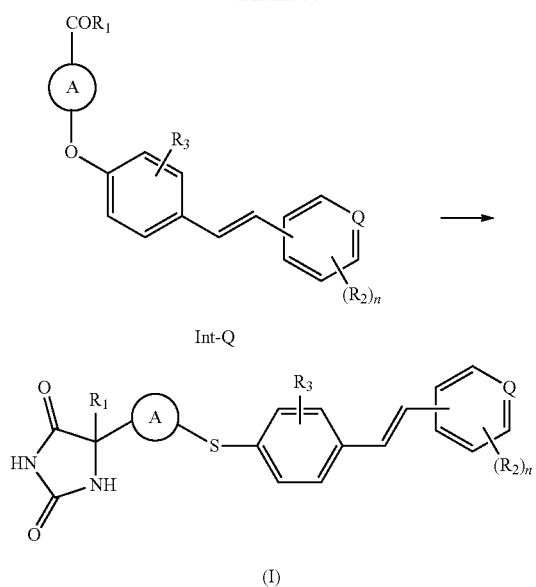

[1]X is halo and the remaining variable group are as defined herein for the compound of formula (I)

To a solution of Int-O is organic solvent is added Int-H, triphenylphospine (PPh$_3$) and palladium(II) acetate. The mixture is stirred and then extracted to obtain Int-P. To a solution of Int-P in an organic solvent is added Int-J and base (e.g., K$_2$CO$_3$). The mixture is extracted to obtain Int-Q. Then Int-Q is reacted with (NH$_4$)$_2$CO$_3$ and potassium cyanide (KCN) in aqueous alcohol to obtain embodiments of the compounds of formula (I) described herein.

General Scheme 4[1]

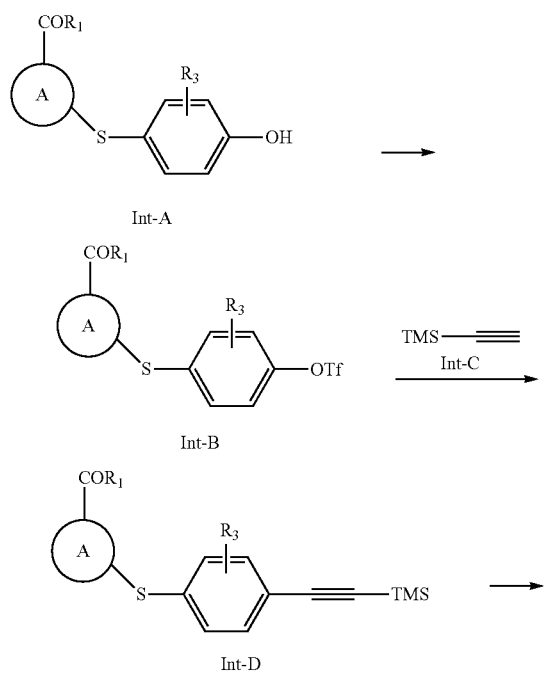

-continued

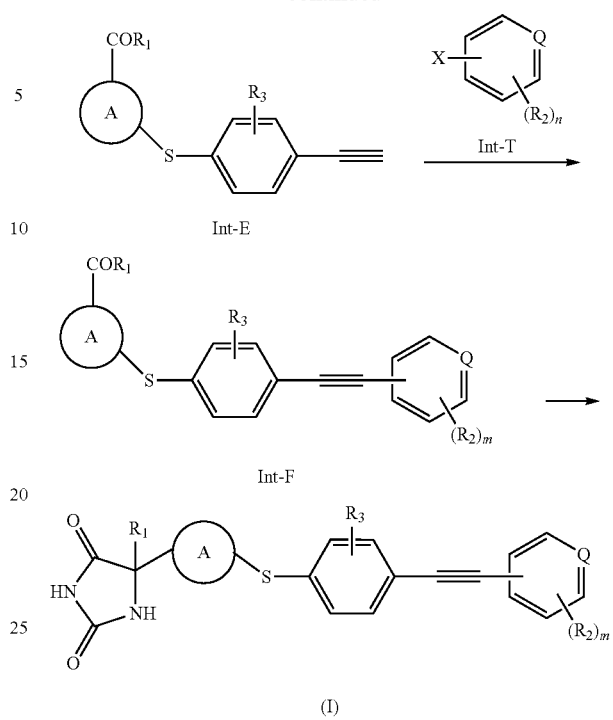

[1]The variable groups are as defined herein for the compounds of formula (I)

(CF$_3$SO$_2$)$_2$O is added to a solution of Int-A in an organic solvent to obtain Int-B. Then, ethynyltrimethylsilane and palladium catalyst are added to a solution of Int-B. After completion of the reaction, the mixture is extracted to obtain Int-D. To a solution of Int-D, Int-T and base (e.g., K$_2$CO$_3$) are added to obtain Int-F. Then, Int-F is reacted with (NH$_4$)$_2$CO$_3$ and potassium cyanide (KCN) in aqueous alcohol to obtain embodiments of the compounds of formula (I) described herein.

General Scheme 5[1]

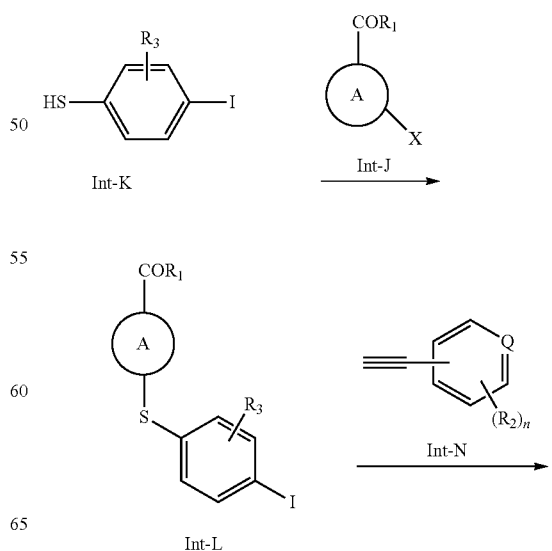

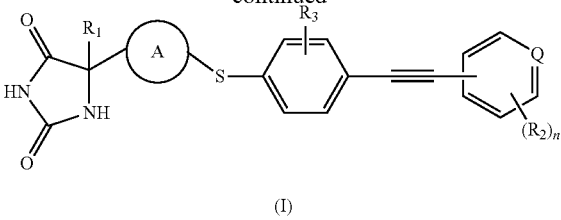

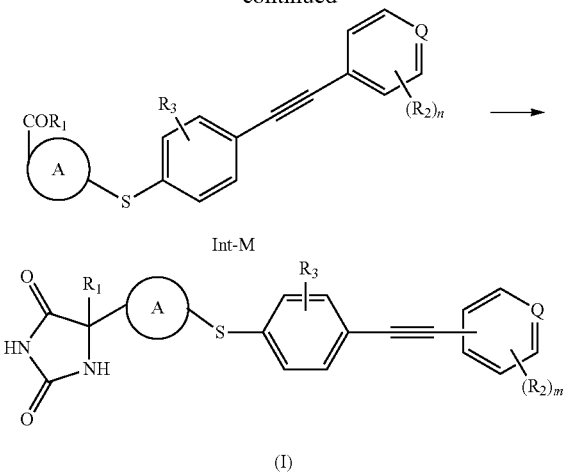

Int-M

[1]X is halo and the remaining variable groups are as defined herein for the compounds of formula (I)

To a solution of Int-K in organic solvent, Int-J and $K_2CO_3$ are added and the mixture is stirred. The reaction mixture is extracted to obtain Int-L. Int-N and a palladium catalyst are added to a solution of Int-L and the reaction mixture is stirred followed by extraction to obtain Int-M. Then, Int-M is reacted with $(NH_4)_2CO_3$ and potassium cyanide (KCN) in aqueous alcohol to obtain embodiments of the compounds of formula (I) described herein.

General Scheme 6[1]

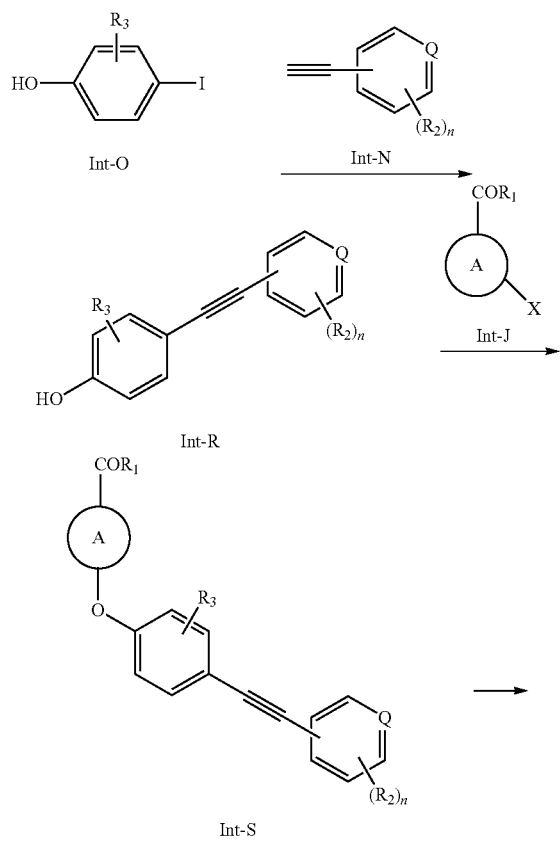

[1]The variable groups are as defined herein for the compounds of formula (I)

To a solution of Int-O is organic solvent is added Int-N, triphenylphospine ($PPh_3$) and palladium catalyst. The mixture is stirred and then extracted to obtain Int-R. To a solution of Int-R in an organic solvent is added Int-J and base (e.g., $K_2CO_3$). The mixture is extracted to obtain Int-S. Then Int-S is reacted with $(NH_4)_2CO_3$ and potassium cyanide (KCN) in aqueous alcohol to obtain embodiments of the compounds of formula (I) described herein.

Nitrogen atoms of the hydantoin moiety of compounds of the application can be alkylated by reacting compounds prepared according to any one of the above General Schemes with sodium hydride and alkyl iodide (e.g., $CH_3I$). Compounds in which X is S(O) or $SO_2$ can be prepared by reacting compounds prepared according to any one of the above General Schemes with m-CPBA.

Pharmaceutically acceptable salts of the compounds described herein can be synthesized from the parent compound containing an acidic or basic moiety by conventional chemical methods. Generally, such salts can be prepared by reacting the free acid or base forms of these compounds with a stoichiometric amount of the appropriate acid or base in water or in an organic solvent, or in a mixture of water and an organic solvent. Examples of suitable organic solvents include, but are not limited to, ether, ethyl acetate, ethanol, isopropanol, and acetonitrile.

Compositions

Another aspect of the application relates to a pharmaceutical composition comprising a compound described herein, or a tautomer, stereoisomer, pharmaceutically acceptable salt, or solvate thereof.

Compositions of the application can also comprise a pharmaceutically acceptable carrier. A pharmaceutically acceptable carrier is non-toxic and should not interfere with the efficacy of the active ingredient. Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the application can be formulated in any matter suitable for administration to a subject to facilitate administration and improve efficacy, including, but not limited to, oral (enteral) administration and parenteral injections. The parenteral injections include intravenous injection or infusion, subcutaneous injection, intradermal injection, and intramuscular injection. Compositions of the application can also be formulated for other routes of administration including transmucosal, ocular, rectal, long acting implantation, sublingual administration, under the tongue, from oral mucosa bypassing the portal circulation, inhalation, or intranasal.

In particular embodiments, compositions are formulated for oral administration.

In yet another aspect, provided is a method of preparing a pharmaceutical composition comprising combining a compound of the application or a tautomer, stereoisomer, pharmaceutically acceptable salt, or solvate thereof, with at least one pharmaceutically acceptable carrier. Pharmaceutical compositions can be prepared by any method known in the art in view of the present disclosure, and one of ordinary skill in the art will be familiar with such techniques used to prepare pharmaceutical compositions. For example, a pharmaceutical composition according to the application can be prepared by mixing a compound of the application with one or more pharmaceutically acceptable carriers according to conventional pharmaceutical compounding techniques, including but not limited to, conventional admixing, dissolving, granulating, emulsifying, encapsulating, entrapping and lyophilizing processes.

Methods of Use

Also provided herein are methods of inhibiting a matrix metalloproteinase (MMP), and treating diseases mediated by MMPs using the compounds and pharmaceutical compositions described herein.

Matrix metalloproteinases (MMPs), also known as matrixins, are a group of enzymes that in concert are responsible for the degradation of most extracellular matrix proteins during organogenesis, growth and normal tissue turnover. MMPs are calcium-dependent zinc-containing endopeptidases, and belong to a larger family of proteases known as the metzincin superfamily. MMPs are capable of degrading extracellular matrix proteins, but can also process a number of bioactive molecules, and are known to be involved in, e.g., cleavage of cell surface receptors, release of apoptotic ligands, and chemokine/cytokine inactivation. MMPs are also thought to play a major role in cell behaviors such as cell proliferation, migration (adhesion/dispersion), differentiation, angiogenesis, apoptosis, and host defense. The MMPs are inhibited by specific endogenous tissue inhibitors of metalloproteinases (TIMPs), which comprise a family of four protease inhibitors: TIMP-1, TIMP-2, TIMP-3, and TIMP-4. Examples of MMPs include, but are not limited to, MMP-1 (Interstitial collagenase), MMP-2 (gelatinase-A), MMP-3 (stromelysin 1), MMP-7 (matrilysin), MMP-8 (neutrophil collagenase), MMP-9 (gelatinase-B), MMP-10 (stromelysin 2), MMP-11 (stromelysin 3), MMP-12 (macrophage elastase), MMP-13 (collagenase 3), MMP-14 (MT1-MMP), etc.

In a preferred embodiment, compounds described herein are capable of inhibiting macrophage elastase (MMP-12) and/or treating diseases mediated by MMP-12. MMP-12, also known as macrophage metalloelastase (MME) or macrophage elastase (ME), is encoded by the MMP12 gene in humans. In other embodiments, compounds described herein are capable of selectively inhibiting MMP-12. The terms "selective," "selectivity," and "selectively" when used with reference to binding or inhibiting the activity of a particular MMP, mean that a compound binds or inhibits the activity of a particular MMP to a greater extent than said compound binds or inhibits the activity of other MMPs. For example, a compound that has selectivity for MMP-12 inhibits the activity of MMP-12 to a greater extent than other MMPs, e.g., MMP-1, MMP-2, MMP-3, MMP-7, MMP-8, MMP-9, MMP-10, MMP-13, MMP-14, etc.

According to embodiments of the application, a compound that is selective for MMP-12 inhibits the activity of MMP-12 by at least about 10-fold, 100-fold, or 1000-fold greater than one or more other MMPs, and preferably inhibits the activity of MMP-12 by at least about 1000-fold greater than at least one other MMP, such as MMP-1 or MMP-7.

Also provided herein are methods of treating a disease mediated by MMP-12. According to embodiments of the application, a method of treating a disease mediated by MMP-12 comprises administering to the subject a therapeutically effective amount of a compound described herein or a tautomer, stereoisomer, pharmaceutically acceptable salt, or solvate thereof, or a pharmaceutical composition described herein.

As used herein, the terms "treat," "treating," and "treatment" are all intended to refer to an amelioration or reversal of at least one measurable physical parameter related to a disease mediated by MMP-12, which is not necessarily discernible in the subject, but can be discernible in the subject. The terms "treat," "treating," and "treatment," can also refer to causing regression, preventing the progression, or at least slowing down the progression of a disease mediated by MMP-12. In a particular embodiment, "treat," "treating," and "treatment" refer to an alleviation, prevention of the development or onset, or reduction in the duration of one or more symptoms associated with a disease mediated by MMP-12. In a particular embodiment, "treat," "treating," and "treatment" refer to prevention of the recurrence of a disease mediated by MMP-12. In a particular embodiment, "treat," "treating," and "treatment" refer to an increase in the survival of a subject having a disease mediated by MMP-12. In a particular embodiment, "treat," "treating," and "treatment" refer to elimination of a disease mediated by MMP-12 in the subject.

As used herein, "a therapeutically effective amount" means an amount of a composition or compound that elicits a biological or medicinal response in a tissue system or subject that is being sought by a researcher, veterinarian, medical doctor or other conditions, which can include alleviation of the symptoms of the disease or disorder being treated. A therapeutically effective amount can vary depending upon a variety of factors, such as the physical condition of the subject, age, weight, health, etc.; and the particular disease to be treated. A therapeutically effective amount can readily be determined by one of ordinary skill in the art in view of the present disclosure.

In particular embodiments of the application, a therapeutically effective amount refers to the amount of a composition or compound described herein which is sufficient to inhibit MMP-12 or treat a disease mediated by MMP-12. Diseases mediated by MMP-12 that can be treated according to the methods described herein include, but are not limited to, asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

EMBODIMENTS

Embodiment 1 is a compound of formula (I):

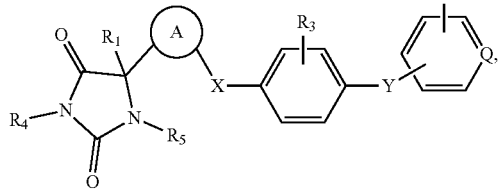

or a tautomer, stereoisomer, pharmaceutically acceptable salt, or solvate thereof,
wherein:
ring A is an optionally substituted heteroaryl;
Q is $CR_2$ or N;
$R_1$ is hydrogen or alkyl;
each $R_2$ is independently hydrogen, alkyl, halo, hydroxyl, haloalkyl, alkoxy, alkylthio, amino, amido, alkylamino, aminoalkyl, cyano, hydroxyalkyl, —$(CH_2)_pC(O)OR_6$, or —$(CH_2)_pOC(O)R_6$;
$R_3$ is hydrogen, halo, or alkyl;
each $R_4$ and $R_5$ is independently hydrogen or alkyl;
each $R_6$ is independently hydrogen or alkyl, wherein the alkyl is unsubstituted or substituted with one or more groups independently selected from amino, hydroxyl, halo, and alkoxy;
X is S or O;
Y is:

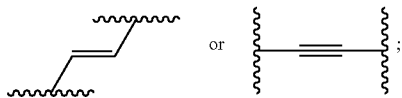

n is 1, 2, 3 or 4; and
p is 0, 1, 2, 3, 4, or 5.

Embodiment 2 is the compound of embodiment 1, wherein ring A is a 5- to 6-membered monocyclic heteroaryl having 1 to 3 heteroatoms independently selected from O, S and N, wherein the 5- to 6-membered monocyclic heteroaryl is optionally substituted with alkyl.

Embodiment 3 is the compound of embodiment 1 or embodiment 2, wherein ring A is a five or six membered monocyclic heteroaryl having 1-2 heteroatoms independently selected from N, S, and O, wherein the 5- to 6-membered monocyclic heteroaryl is optionally substituted with alkyl.

Embodiment 4 is the compound of embodiment 2 or 3, wherein the 5- to 6-membered monocyclic heteroaryl is optionally substituted with —$CH_3$.

Embodiment 5 is the compound of any one of embodiments 1-4, wherein ring A is furanyl.

Embodiment 6 is the compound of any one of embodiments 1-4, wherein ring A is pyridinyl.

Embodiment 7 is the compound of any one of embodiments 1-4, wherein ring A is thienyl.

Embodiment 8 is the compound of any one of embodiments 1-4, wherein ring A is N-methyl pyrazolyl.

Embodiment 9 is the compound of any one of embodiments 1-4, wherein ring A is:

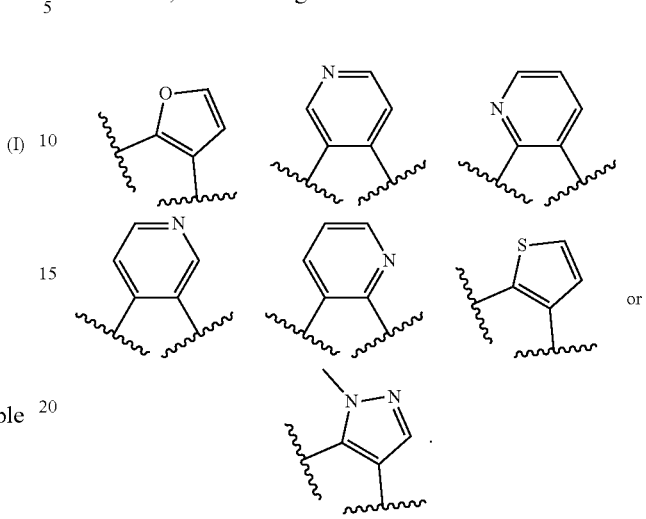

Embodiment 10 is the compound of embodiment 5, being a compound of formula (II):

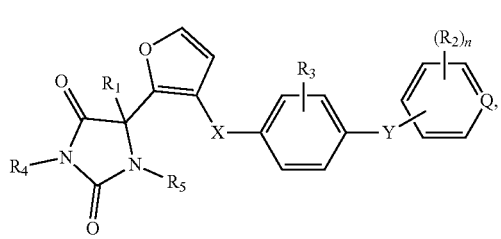

or a tautomer, stereoisomer, pharmaceutically acceptable salt, or solvate thereof,
wherein each of the variables are as defined above for the compound of formula (I).

Embodiment 11 is the compound of embodiment 6, being a compound of formula (III):

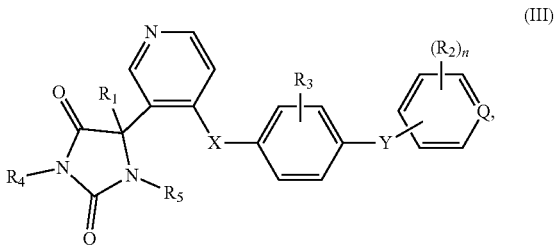

or a tautomer, stereoisomer, pharmaceutically acceptable salt, or solvate thereof,
wherein each of the variables is as defined in the compound of formula (I).

Embodiment 12 is the compound of embodiment 7, being a compound of formula (IV):

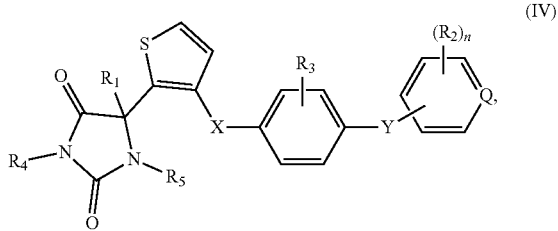

(IV)

or a tautomer, stereoisomer, pharmaceutically acceptable salt, or solvate thereof,
wherein each of the variables is as defined in the compound of formula (I).

Embodiment 13 is the compound of embodiment 8, being a compound of formula (V):

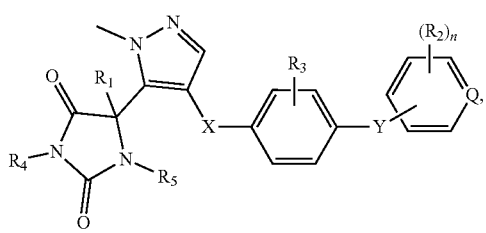

(V)

or a tautomer, stereoisomer, pharmaceutically acceptable salt, or solvate thereof,
wherein each of the variables are as defined above for the compound of formula (I).

Embodiment 14 is the compound of any one of embodiments 1 to 13, wherein $R_1$ is hydrogen.

Embodiment 15 is the compound of any one of embodiments 1 to 13, wherein $R_1$ is $C_{1-4}$ alkyl.

Embodiment 16 is the compound of embodiment 15, wherein $R_1$ is —$CH_3$ or —$CH_2CH_3$.

Embodiment 17 is the compound of any one of embodiments 1-16, wherein $R_3$ is hydrogen.

Embodiment 18 is the compound of any one of embodiments 1-17, wherein $R_4$ is hydrogen.

Embodiment 19 is the compound of any one of embodiments 1-18, wherein $R_5$ is hydrogen.

Embodiment 20 is the compound of any one of embodiments 1-19, wherein X is S.

Embodiment 21 is the compound of any one of embodiments 1-19, wherein X is O.

Embodiment 22 is the compound of any one of embodiments 1-21, wherein Q is N.

Embodiment 23 is the compound of any one of embodiments 1-22, wherein

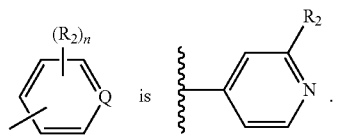

Embodiment 24 is the compound of any one of embodiments 1-21, wherein Q is $CR_2$.

Embodiment 25 is the compound of any one of embodiments 1-24, wherein $R_2$ is $C_{1-3}$ alkoxy (e.g., -$OCH_3$, —$OCH_2CH_2CH_3$, —$OCH_2CH_3$, —$OCH(CH_3)_2$), $C_{1-4}$ alkyl (e.g., —$CH_3$, —$CH_2CH_3$, —$CH_2CH(CH_3)_2$), —$CH_2OH$, —OH, —COOH, —$C(O)NH_2$, —$C(O)NHCH_3$, or —$CH_2OC(O)CH(NH_2)CH(CH_3)_2$, —$C(O)NH_2$, or —$C(O)NHCH_3$.

Embodiment 26 is the compound of embodiment 25, wherein $R_2$ is —$CH_3$, —$C(O)NH_2$, —$CH_2OH$, —$OCH_3$, or OH.

Embodiment 27 is the compound of embodiment 26, wherein $R_2$ is —$CH_3$.

Embodiment 28 is the compound of any one of embodiments 1 to 27, wherein $R_2$ is —$CH_3$.

Embodiment 29 is the compound of any one of embodiments 1-21, wherein

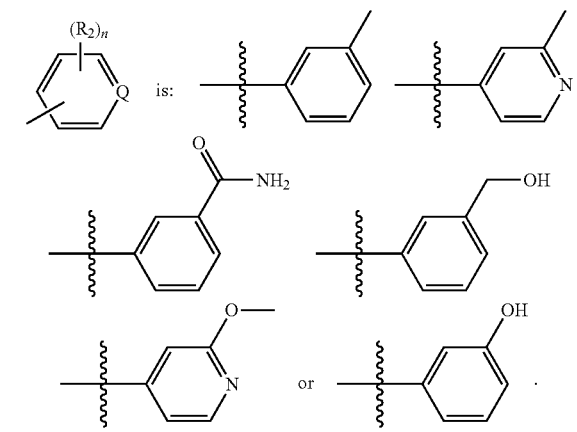

Embodiment 30 is the compound of any one of embodiments 1-29, wherein Y is:

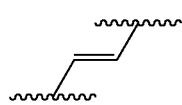

Embodiment 31 is the compound of any one of embodiments 1-29, wherein Y is:

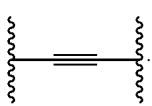

Embodiment 32 is the compound of embodiment 1, wherein:
ring A is pyridinyl;
$R_1$ is hydrogen, —$CH_3$ or —$CH_2CH_3$;
$R_2$ is —$CH_3$, —$C(O)NH_2$, —$CH_2OH$, —$OCH_3$, or —OH;
each of $R_3$, $R_4$, and $R_5$ is hydrogen;
X is S or O;
Y is

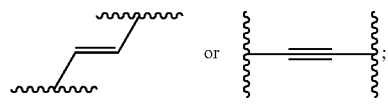

Q is CH or N; and
n is 1.

Embodiment 33 is the compound of embodiment 1, wherein:
ring A is furanyl;
$R_1$ is hydrogen, —$CH_3$ or —$CH_2CH_3$;
$R_2$ is —$CH_3$, —C(O)$NH_2$, —$CH_2OH$, —$OCH_3$, or —OH;
each of $R_3$, $R_4$, and $R_5$ is hydrogen;
X is S or O;
Y is

[structure: alkene or alkyne linker];

Q is CH or N; and
n is 1.

Embodiment 34 is the compound of embodiment 1, wherein:
ring A is thienyl;
$R_1$ is hydrogen, —$CH_3$ or —$CH_2CH_3$;
$R_2$ is —$CH_3$, —C(O)$NH_2$, —$CH_2OH$, —$OCH_3$, or —OH;
each of $R_3$, $R_4$, and $R_5$ is hydrogen;
X is S or O;
Y is

[structure: alkene or alkyne linker];

Q is CH or N; and
n is 1.

Embodiment 35 is the compound of embodiment 1:
ring A is N-methyl pyrazolyl;
$R_1$ is hydrogen, —$CH_3$ or —$CH_2CH_3$;
$R_2$ is —$CH_3$, —C(O)$NH_2$, —$CH_2OH$, —$OCH_3$, or —OH;
each of $R_3$, $R_4$, and $R_5$ is hydrogen;
X is S or O;
Y is

[structure: alkene or alkyne linker];

Q is CH or N; and
n is 1.

Embodiment 36 is a compound selected from the group consisting of:

[chemical structures]

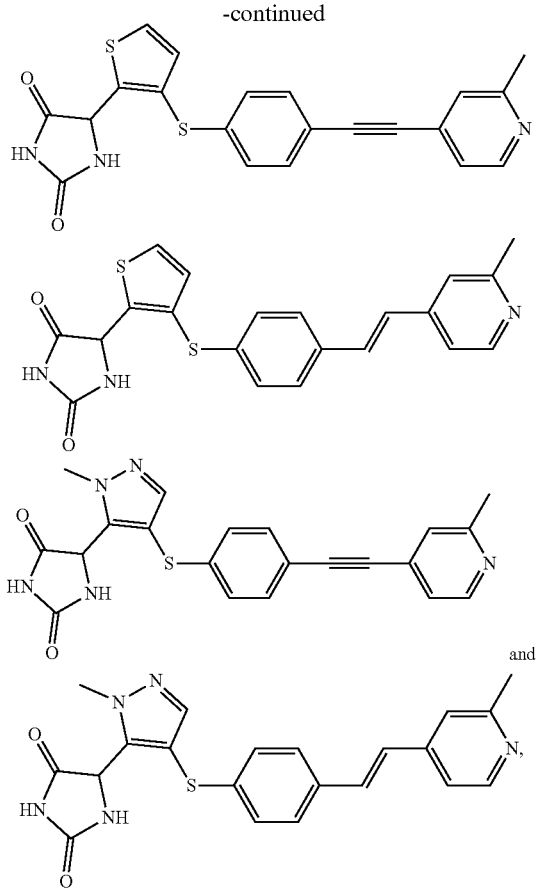

or a tautomer, stereoisomer, pharmaceutically acceptable salt, or hydrate thereof.

Embodiment 37 is the compound of embodiment 36, or a pharmaceutically acceptable salt thereof.

Embodiment 38 is a pharmaceutical composition comprising the compound of any one of embodiments 1-37, and at least one pharmaceutically acceptable carrier.

Embodiment 39 is a method of inhibiting macrophage elastase (MMP-12) in a subject in need thereof, the method comprising administering to the subject the pharmaceutical composition of embodiment 38.

Embodiment 40 is a method of treating a disease mediated by macrophage elastase (MMP-12) in a subject in need thereof, the method comprising administering to the subject the pharmaceutical composition of embodiment 38.

Embodiment 41 is the method of embodiment 40, wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 42 is the compound of any one of embodiments 1-37, or the pharmaceutical composition of embodiment 38 for use in inhibiting macrophage elastase (MMP-12).

Embodiment 43 is the compound of any one of embodiments 1-37, or the pharmaceutical composition of embodiment 38 for use treating a disease mediated by macrophage elastase (MMP-12).

Embodiment 44 is the compound or composition for use of embodiment 43, wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 45 is use of the compound of any one of embodiments 1-37, or the pharmaceutical composition of embodiment 38 in the manufacture of a medicament for inhibiting macrophage elastase (MMP-12).

Embodiment 46 is use of the compound of any one of embodiments 1-37, or the pharmaceutical composition of embodiment 38 in the manufacture of a medicament for treating a disease mediated by macrophage elastase (MMP-12).

Embodiment 47 is use of embodiment 46, wherein wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 48 is a method of preparing the pharmaceutical composition of embodiment 38, comprising combining the compound or a pharmaceutically acceptable salt thereof with at least one pharmaceutically acceptable carrier.

EXAMPLES

The following examples of the application are to further illustrate the nature of the application. It should be understood that the following examples do not limit the application and the scope of the application is to be determined by the appended claims.

Methods of Synthesis

Unless indicated otherwise, the abbreviations for chemical reagents and synthesis conditions have their ordinary meaning known in the art as follows:

"LDA" refers to lithium diisopropyl amide;
"EA" refers to ethyl acetate;
"PE" refers to petroleum ether;
"r.t." and "rt" refer to room temperature;
"THF" refers to tetrahydrofuran;
"DEAD" refers to diethyl azodicarboxylate;
"TBAB" refers to tetrabutylammonium bromide;
"DCM" refers to dichloromethane;
"HOBT" refers to hydroxybenzotriazole;
"LAH" refers to lithium aluminum hydride;
"Tf$_2$O" refers to trifluoromethanesulfonic anhydride'
"TLC" refers to thin layer chromatography;
"Prep-TLC" refers to preparatory thin layer chromatography;
"TMS-I" refers to trimethylsilyl iodide;
"Hex" refers to hexanes;
"DMF" refers to dimethylformamide;
"h" refers to hours;
"HG-II" and "Hoveyda-Grubbs II" refer to (1,3-Bis-(2,4,6-trimethylphenyl)-2-imidazolidinylidene)dichloro(o-isopropoxyphenylmethylene)ruthenium;
"EDCI" refers to 1-Ethyl-3-(3-dimethylaminopropyl)carbodiimide;
"DMAP" refers to 4-Dimethylaminopyridine;

"Prep-HPLC" refers to preparative high performance liquid chromatography;
"DHP" refers to dihydropyran;
"DPPF" refers to 1,1'-Bis(diphenylphosphino)ferrocene; and
"DIEA" refers to diisopropylethylamine.

Example 1: Preparation of Compound AC-1

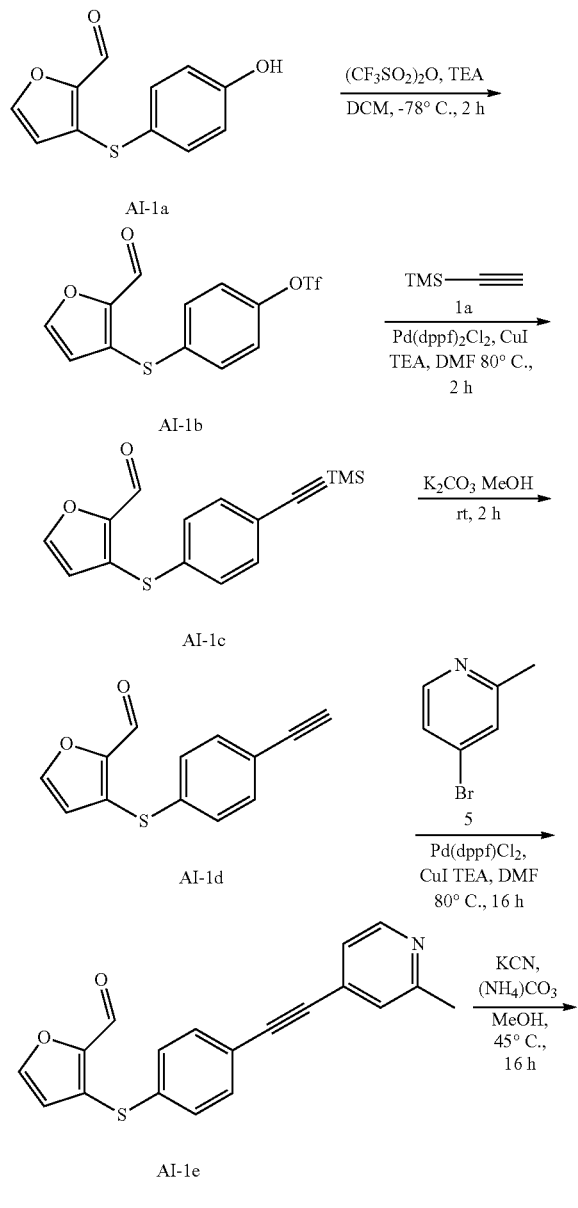

To a solution of AI-1a (13.9 g, 63.11 mmol, 1.0 eq) in DCM (500 mL) was added TEA (20.63 g, 189.34 mmol, 3 eq) and (CF$_3$SO$_2$)$_2$O (19.59 g, 69.42 mmol, 1.1 eq) at −78° C. under nitrogen atmosphere. The mixture was stirred at −78° C. for 2 h under nitrogen atmosphere. Then the mixture was warmed to 0° C. and quenched with saturated Na$_2$CO$_3$ (200 mL) solution. The organic phases were washed with brine, dried over anhydrous Na$_2$SO$_4$ and concentrated under reduced pressure. The residue was purified by silica gel chromatography to afford AI-1b (9.7 g, 44%).

To a solution of AI-1b (5.48 g, 15.57 mmol, 1.0 eq) and ethynyltrimethylsilane (1.84 g, 18.68 mmol, 1.1 eq) in DMF (150 mL) was added TEA (4.72 g, 46.71 mmol, 3 eq), Pd(dppf)$_2$Cl$_2$ (1.4 g, 2 mmol, 0.2 eq) and CuI (0.29 g, 1.56 mmol, 0.1 eq) under nitrogen atmosphere. The mixture was stirred at 80° C. for 2 h under nitrogen atmosphere. Then the mixture was quenched with saturated NH$_4$Cl (300 mL) solution and extracted with ethyl acetate (100 mL*3). The combined organic phases were washed with brine, dried over anhydrous Na$_2$SO$_4$ and concentrated under reduced pressure. The residue was purified by silica gel chromatography to afford AI-1c (1.6 g, 34%).

To a mixture of AI-1c (1.6 g, 23.3 mmol, 1.0 eq) in methanol (100 mL) was added K$_2$CO$_3$ (3.22 g, 23.3 mmol, 3 eq). The mixture was stirred at room temperature for 2 h under nitrogen atmosphere. Then the mixture was quenched with H$_2$O (100 mL), and extracted with ethyl acetate (50 mL*3). The combined organic phases were washed with brine, dried over anhydrous Na$_2$SO$_4$ and concentrated under reduced pressure. The residue was purified by silica gel chromatography to afford AI-1d (1.37 g, 99%).

To a solution of AI-1d (1.17 g, 5.13 mmol, 1.0 eq) and 4-bromo-2-methylpyridine (0.88 g, 5.13 mmol, 1.0 eq) in DMF (30 mL) was added TEA (1.55 g, 15.3 mmol, 3 eq), Pd(dppf)$_2$Cl$_2$ (0.38 g, 0.51 mmol, 0.1 eq) and CuI (97 mg, 0.51 mmol, 0.1 eq) under nitrogen atmosphere. The mixture was stirred at 80° C. for 16 h under nitrogen atmosphere. Then the mixture was quenched with saturated NH$_4$Cl (100 mL) solution, and extracted with ethyl acetate (30 mL*3). The combined organic phases were washed with brine, dried over anhydrous Na$_2$SO$_4$ and concentrated under reduced pressure. The residue was purified by silica gel chromatography to afford AI-1e (0.8 g, 49%).

To a solution of AI-1e (800 mg, 2.5 mmol, 1.0 eq) in MeOH (20 mL) was added (NH$_4$)$_2$CO$_3$ (963 mg, 10.03 mmol, 4.0 eq) and KCN (326 mg, 5.02 mmol, 2.0 eq). The mixture was stirred at 45° C. for 16 h. To the reaction was added 3 M HCl to adjust pH=1-2 and stirred at room temperature for 1 h. Then a saturated aqueous solution of NaHCO$_3$ was added to adjust pH=7-8 and the reaction was extracted with ethyl acetate. The organic layer was washed with brine, dried over anhydrous Na$_2$SO$_4$ and concentrated under reduced pressure. The residue was purified by silica gel chromatography to give AC-1 (300 mg, 58%) as a yellow solid.

Example 2: Preparation of Compound AC-2

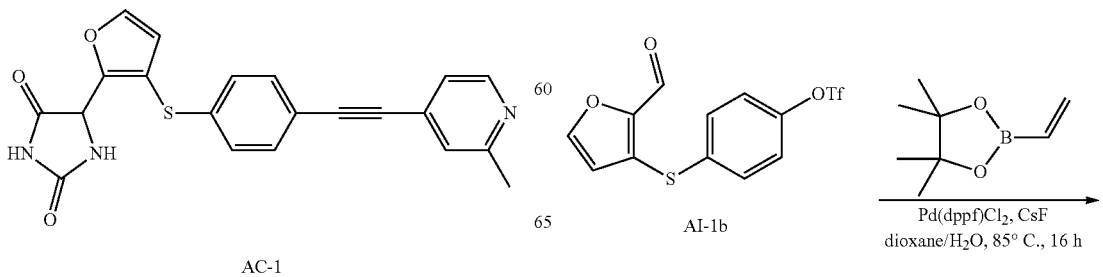

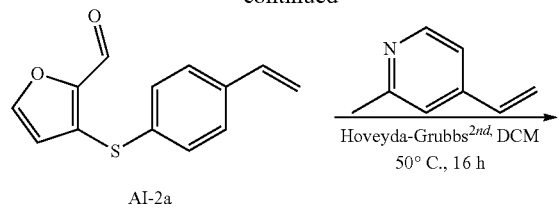

AI-2a

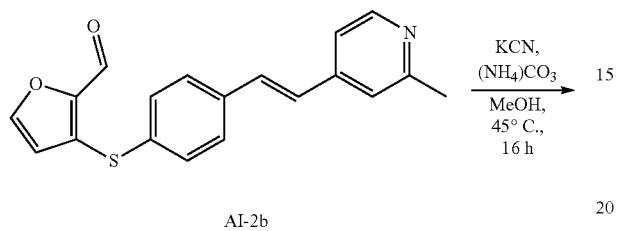

AI-2b

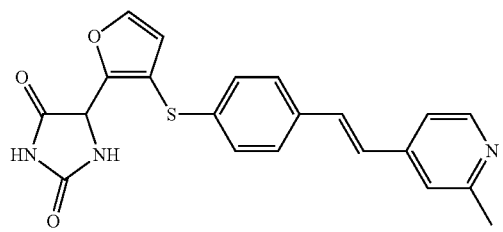

AC-2

To a solution of AI-1b (2.5 g, 7.12 mmol, 1.0 eq) in dioxane/$H_2O$ (5/1, 60 mL) was successively added 4,4,5,5-tetramethyl-2-vinyl-1,3,2-dioxaborolane (1.2 g, 7.83 mmol, 1.1 eq), Pd(dppf)$_2$Cl$_2$ (0.52 g, 0.71 mmol, 0.1 eq) and CsF (2.8 g, 15.45 mmol, 2 eq) under nitrogen atmosphere. The mixture was stirred at 85° C. for 16 h. Then the reaction was cooled to room temperature and quenched with $H_2O$ (50 mL) and extracted with ethyl acetate (30 mL*3). The combined organic phases were washed with brine, dried over anhydrous $Na_2SO_4$ and concentrated under reduced pressure. The residue was purified by silica gel chromatography to afford AI-2a (1.3 g, 79%).

To a solution of AI-2a (1.3 g, 5.65 mmol, 1.0 eq) in DCM (50 mL) was added 2-methyl-4-vinylpyridine (0.74 g, 6.21 mmol, 1.1 eq) and HG-II (354 g, 0.57 mmol, 0.1 eq). The mixture was stirred at 50° C. for 14 h under nitrogen atmosphere. Then the mixture was diluted with DCM (100 mL) and washed with brine, dried over anhydrous $Na_2SO_4$ and concentrated under reduced pressure. The residue was purified by silica gel chromatography to afford AI-2b (0.3 g, 16%).

To a solution of AI-2b (330 mg, 1.0 mmol, 1.0 eq) in MeOH (10 mL) was added $(NH_4)_2CO_3$ (393 mg, 4 mmol, 4.0 eq) and KCN (133 mg, 2.0 mmol, 2.0 eq). The mixture was stirred at 45° C. for 16 h. The reaction was added with 3 M HCl to adjust pH=1-2 and stirred at room temperature for 1 h, then saturated aqueous of $NaHCO_3$ was added to adjust pH=7-8 and the reaction was extracted with ethyl acetate. The organic layer was washed with brine, dried over anhydrous $Na_2SO_4$ and concentrated under reduced pressure. The residue was purified by silica gel chromatography to give AC-2 (116 mg, 29%) as a yellow solid.

Example 3: Preparation of Compound AC-3

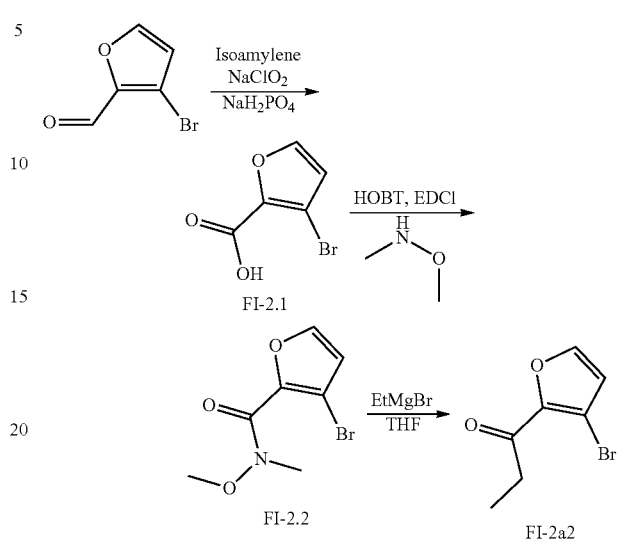

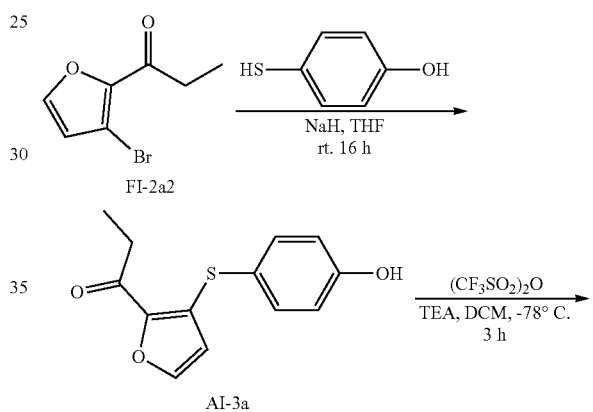

AI-3a

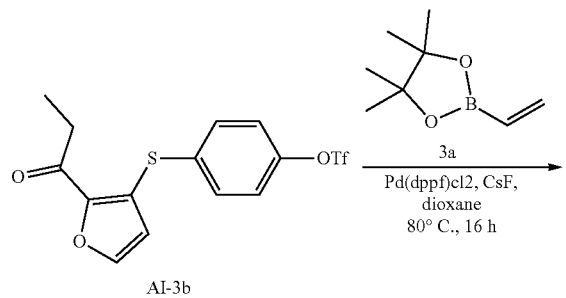

AI-3b

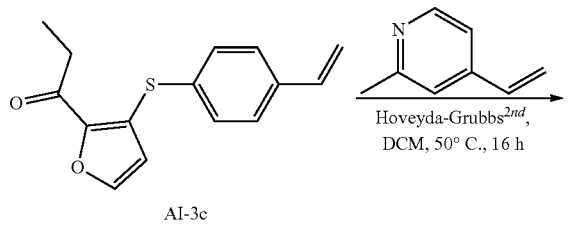

AI-3c

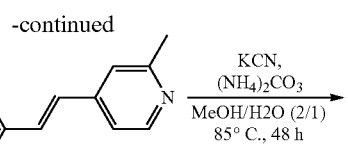

AI-3d

HN–[structure]–NH
O  O
AC-3

To a solution of 3-bromofuran-2-carbaldehyde (5 g, 30.9 mmol, 1.0 eq) and isoamylene (9 mL, 77.2 mmol, 2.5 eq) in tert-butanol (50 mL) was added a solution of NaClO$_2$ (8.1 g, 89.6 mmol, 3.0 eq) and NaH$_2$PO$_4$.2H$_2$O (10.3 g, 67.9 mmol, 2.2 eq) in H$_2$O (70 mL) slowly. The mixture was stirred at room temperature for 16 h. The mixture was concentrated under reduced pressure and diluted with H$_2$O. Then 1 M HCl was added to the mixture to adjust pH=1 and filtered to afford compound FI-2.1 (6.2 g, 100%).

To a mixture of compound FI-2.1 (5 g, 26.46 mmol, 1.0 eq) and TEA (8 g, 79.37 mmol, 3.0 eq) was added N,O-dimethylhydroxylamine (5.16 g, 52.91 mmol, 2.0 eq), HOBT (3.93 g, 29.1 mmol, 1.1 eq) and EDCI (6.06 g, 31.75 mmol, 1.2 eq). The mixture was stirred for 5 h. Then the mixture was diluted with water and extracted with ethyl acetate. The organic phase was dried over anhydrous Na$_2$SO$_4$ and concentrated under reduced pressure. The residue was purified by silica gel chromatography to afford compound FI-2.2 (4.3 g, 67%).

To a mixture of compound FI-2.2 (1 g, 4.29 mmol, 1.0 eq) in dry THF (10 mL) was added EtMgBr (1.0 mol/L in THF, 8.6 mL, 8.58 mmol, 2.0 eq) dropwise at 0° C. under nitrogen atmosphere. The mixture was stirred at 0° C. for 1 h. The reaction was quenched with saturated aqueous NH$_4$Cl and extracted with ethyl acetate (3×50 mL). The combined organic layers were washed with brine and water, dried over Na$_2$SO$_4$ and concentrated under vacuum. The residue was purified by column chromatography on a silica gel to give compound FI-2a2 (0.6 g, 69%).

To a mixture of FI-2a2 (600 mg, 2.97 mmol, 1.0 eq) and 4-mercaptophenol (450 mg, 2.97 mmol, 1.0 eq) in THF (10 mL) was added NaH (143 mg, 3.56 mmol, 1.2 eq) at 0° C. The mixture was allowed to warm to room temperature and stirred for 16 h under nitrogen atmosphere. Then the mixture was concentrated to half solvent and then 2 N HCl was added to adjust pH=6. The reaction was filtered and the filtrate was concentrated. The residue was purified by column chromatography on a silica gel to give AI-3a (750 mg, 99%).

To a solution of AI-3a (3.7 g, 14.9 mmol, 1.0 eq) in DCM (150 mL) was added TEA (4.52 g, 44.75 mmol, 3 eq) and (CF$_3$SO$_2$)$_2$O (6.3 g, 22.37 mmol, 1.5 eq) at −78° C. under nitrogen atmosphere. The mixture was stirred at −78° C. for 2 h under nitrogen atmosphere. Then the mixture was warmed to 0° C. and quenched with saturated Na$_2$CO$_3$ (200 mL) solution. The organic phases were washed with brine, dried over anhydrous Na$_2$SO$_4$ and concentrated under reduced pressure. The residue was purified by silica gel chromatography to afford AI-3b (4.05 g, 71%).

To a solution of AI-3b (4.05 g, 10.65 mmol, 1.0 eq) in dioxane/H$_2$O (5/1, 100 mL) was successively added 4,4,5,5-tetramethyl-2-vinyl-1,3,2-dioxaborolane (1.8 g, 11.72 mmol, 1.1 eq), Pd(dppf)$_2$Cl$_2$ (0.78 g, 1.06 mmol, 0.1 eq) and CsF (3.24 g, 21.3 mmol, 2 eq) under nitrogen atmosphere. The mixture was stirred at 85° C. for 16 h. Then the reaction was cooled to room temperature and quenched with H$_2$O (200 mL) and extracted with ethyl acetate (60 mL*3). The combined organic phases were washed with brine, dried over anhydrous Na$_2$SO$_4$ and concentrated under reduced pressure. The residue was purified by silica gel chromatography to afford AI-3c (2.37 g, 86%).

To a solution of AI-3c (2.37 g, 9.18 mmol, 1.0 eq) in DCM (100 mL) was added 2-methyl-4-vinylpyridine (1.2 g, 10.1 mmol, 1.0 eq) and HG-II (575 mg, 0.9 mmol, 0.1 eq). The mixture was stirred at 50° C. for 14 h under nitrogen atmosphere. Then the mixture was diluted with DCM (100 mL) and washed with brine, dried over anhydrous Na$_2$SO$_4$ and concentrated under reduced pressure. The residue was purified by silica gel chromatography to afford AI-3d (0.55 g, 17%).

To a solution of AI-3d (550 mg, 1.57 mmol, 1.0 eq) in MeOH/H$_2$O (12 mL, 5/1) was added (NH$_4$)$_2$CO$_3$ (605 mg, 6.3 mmol, 4.0 eq) and KCN (204 mg, 3.15 mmol, 2.0 eq). The mixture was stirred at 45° C. for 16 h. The reaction was added with 3 M HCl to adjust pH=1-2 and stirred at room temperature for 1 h. Then a saturated aqueous solution of NaHCO$_3$ was added to adjust pH=7-8 and extracted with ethyl acetate. The organic layer was washed with brine, dried over anhydrous Na$_2$SO$_4$ and concentrated under reduced pressure. The residue was purified by silica gel chromatography to give AC-3 (90 mg, 13%) as a yellow solid.

Example 4: Preparation of Compound AC-4

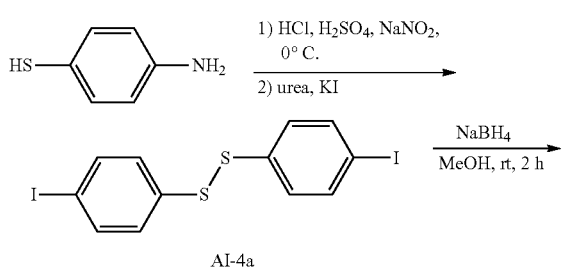

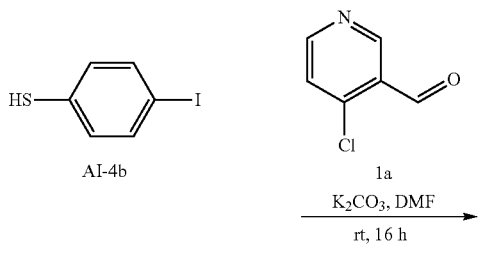

-continued

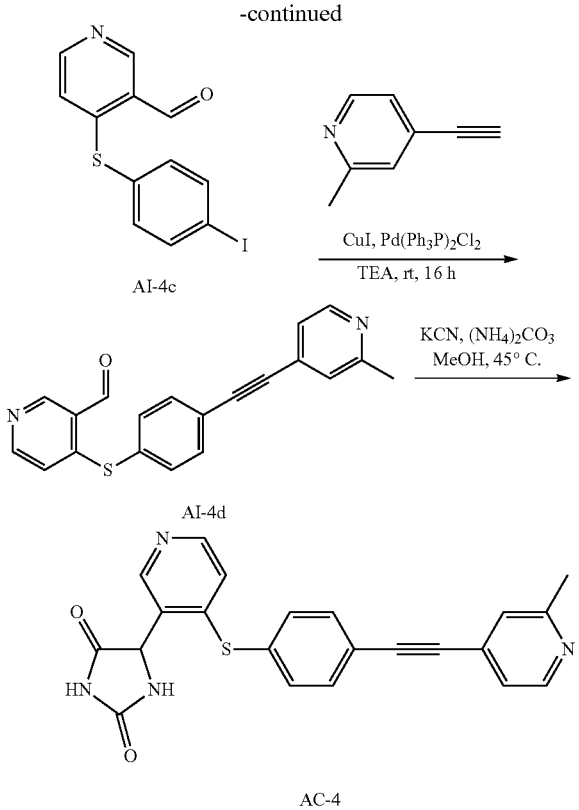

AI-4c

AI-4d

AC-4

To a solution of 4-aminothiophenol (10 g, 79.87 mmol, 1.0 eq) in H$_2$O (80 mL) was successively added HCl (80 mL), H$_2$SO$_4$ (30 mL) and NaNO$_2$ (6.6 g, 95.84 mmol, 1.2 eq) at 0° C. The mixture was stirred at 0° C. for 0.5 h. Then urea (0.46 g, 7.99 mmol, 0.1 eq) was added. After 15 min, a solution of KI (26.5 g, 159.74 mmol, 2.0 eq) in H$_2$O (1.5 L) was drop wise added at 0° C. The mixture was stirred at 0° C. for 5 h. Then the mixture was extracted with ethyl acetate. The organic layer was washed with brine, dried over anhydrous Na$_2$SO$_4$ and concentrated under reduced pressure. The residue was purified by silica gel chromatography to afford AI-4a (7.3 g, 39%).

A mixture of AI-4a (1.8 g, 3.83 mmol, 1.0 eq) in MeOH (40 mL) was stirred at room temperature for 2 h. The reaction mixture was concentrated under reduced pressure. The residue was diluted with ethyl acetate (50 mL) and washed with water and brine. The organic layer was dried over anhydrous Na$_2$SO$_4$ and concentrated under reduced pressure. The residue was purified by silica gel chromatography to afford AI-4b (0.9 g, 50%).

To a solution of AI-4b (230 mg, 1 mmol, 1.0 eq) in DMF (10 mL) was added 4-chloronicotinaldehyde (140 mg, 1 mmol, 1.0 eq) and K$_2$CO$_3$ (276 mg, 2 mmol, 2.0 eq). The mixture was stirred at room temperature for 16 h. Then water (30 mL) was added and extracted with ethyl acetate (20 mL×3). The organic layer was washed with brine, dried over anhydrous Na$_2$SO$_4$ and concentrated under reduced pressure. The residue was purified by silica gel chromatography to afford AI-4c (0.3 g, 88%).

To a solution of AI-4c (1 g, 2.9 mmol, 1.0 eq) and 4-ethynyl-2-methylpyridine (0.41 g, 3.5 mmol, 1.2 eq) in TEA (1.19 g, 29 mmol, 0.1 eq) was added Pd(Ph$_3$P)$_2$Cl$_2$ (0.21 g, 0.29 mmol, 0.1 eq) and CuI (0.06 g, 0.29 mmol, 0.1 eq) under nitrogen atmosphere. The mixture was stirred at room temperature for 16 h under nitrogen atmosphere. Then the mixture was quenched with saturated NH$_4$Cl solution. The mixture was extracted with ethyl acetate. The combined organic phases were washed with brine, dried over anhydrous Na$_2$SO$_4$ and concentrated under reduced pressure. The residue was purified by silica gel chromatography to afford AI-4d (0.8 g, 83%).

To a solution of AI-4d (0.2 g, 0.61 mmol, 1.0 eq) in methanol (10 mL) was added Pd/C (20 mg). The mixture was stirred under hydrogen atmosphere (20 psi) at room temperature for 16 h. After filtering, the filtrate was concentrated to give AI-4e (170 mg, 84%) without further purification.

To a solution of compound AI-4e (130 mg, 0.39 mmol, 1.0 eq) in MeOH (3 mL) was added (NH$_4$)$_2$CO$_3$ (151 mg, 1.57 mmol, 4.0 eq) and KCN (50 mg, 0.78 mmol, 2.0 eq). The mixture was stirred at 45° C. for 16 h. The reaction was added with 3 M HCl to adjust pH=1-2 and stirred at room temperature for 1 h, then a saturated aqueous solution of NaHCO$_3$ was added to adjust pH=7-8 and extracted with ethyl acetate. The organic layer was washed with brine, dried over anhydrous Na$_2$SO$_4$ and concentrated under reduced pressure. The residue was purified by prep-TLC to give AC-4 (64 mg, 41%) as a white solid.

Example 5: Preparation of Compound AC-5

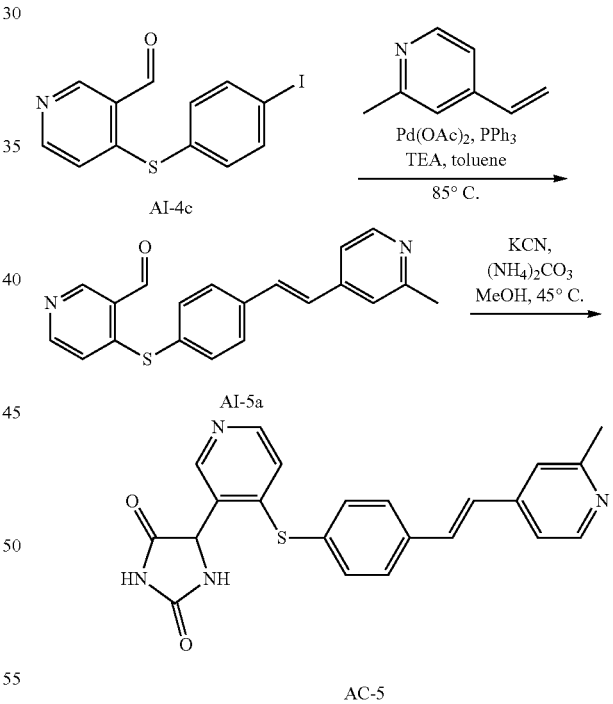

AI-4c

AI-5a

AC-5

To a solution of compound AI-4c (1.1 g, 3.22 mmol, 1.0 eq) in toluene (70 mL) was successively added 2-methyl-4-vinylpyridine (0.77 g, 6.45 mmol, 2.0 eq), PPh$_3$ (84 mg, 0.32 mmol, 0.1 eq), TEA (0.98 g, 9.67 mmol, 3 eq) and Pd(OAc)$_2$ (84 mg, 0.32 mmol, 0.1 eq) under nitrogen atmosphere. The mixture was stirred at 100° C. for 16 h. Then the reaction was cooled to room temperature and quenched with saturated NH$_4$Cl solution. The mixture was extracted with ethyl acetate. The combined organic phases were washed with brine, dried over anhydrous Na$_2$SO$_4$ and concentrated under reduced pressure. The residue was purified by silica gel chromatography to afford AI-5a (0.24 g, 23%).

To a solution of AI-5a (220 mg, 0.66 mmol, 1.0 eq) in MeOH (6 mL) was added (NH$_4$)$_2$CO$_3$ (254 mg, 2.65 mmol, 4.0 eq) and KCN (86 mg, 1.32 mmol, 2.0 eq). The mixture was stirred at 45° C. for 16 h. The reaction was added 3 M HCl to adjust pH=1-2 and stirred at room temperature for 1 h, then a saturated aqueous solution of NaHCO$_3$ was added to adjust pH=7-8 and extracted with ethyl acetate. The organic layer was washed with brine, dried over anhydrous Na$_2$SO$_4$ and concentrated under reduced pressure. The residue was purified by prep-TLC to give AC-5 (60 mg, 23%) as a white solid.

Example 6: Preparation of Compound AC-6

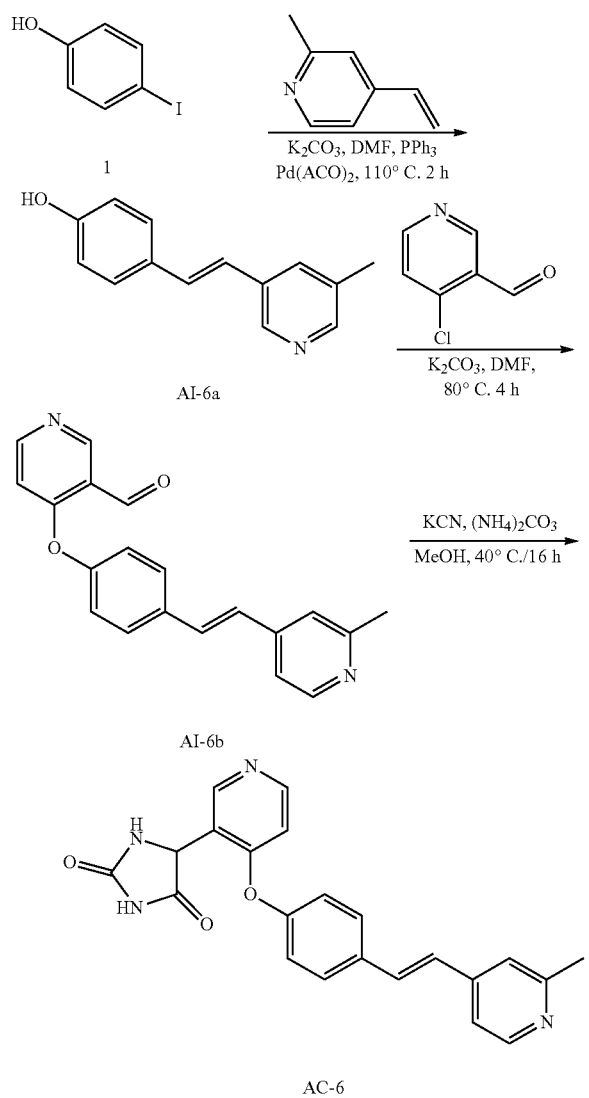

cooled to room temperature and quenched with saturated NH$_4$Cl solution. The mixture was extracted with ethyl acetate. The combined organic phases were washed with brine, dried over anhydrous Na$_2$SO$_4$ and concentrated under reduced pressure. The residue was purified by silica gel chromatography to afford compound AI-6a (0.31 g, 64%).

To a solution of compound AI-6a (0.94 g, 4.45 mmol, 1.0 eq) in DMF (50 mL) was added 4-chloronicotinaldehyde (0.63 g, 3.82 mmol, 1.0 eq) and K$_2$CO$_3$ (1.22 g, 8.9 mmol, 2 eq). The mixture was stirred at 80° C. for 4 h. Then the mixture was diluted with water (100 mL) and extracted with ethyl acetate (50 mL*3). The organic layer was washed with brine, dried over anhydrous Na$_2$SO$_4$ and concentrated under reduced pressure. The residue was purified by silica gel chromatography to afford compound AI-6b (0.7 g, 49%).

To a solution of compound AI-6b (1.95 g, 6.16 mmol, 1.0 eq) in MeOH (30 mL) was added (NH$_4$)$_2$CO$_3$ (2.37 g, 24.65 mmol, 4.0 eq) and KCN (0.8 g, 12.32 mmol, 2.0 eq). The mixture was stirred at 45° C. for 16 h. To the reaction was added 3 M HCl to adjust pH=1-2 and stirred at room temperature for 1 h, then saturated aqueous of NaHCO$_3$ was added to adjust pH=7-8 and extracted with ethyl acetate. The organic layer was washed with brine, dried over anhydrous Na$_2$SO$_4$ and concentrated under reduced pressure. The residue was purified by silica gel chromatography to give AI-6 (1.49 g, 61%) as a white solid.

Example 7: Synthesis of Compound AC-7

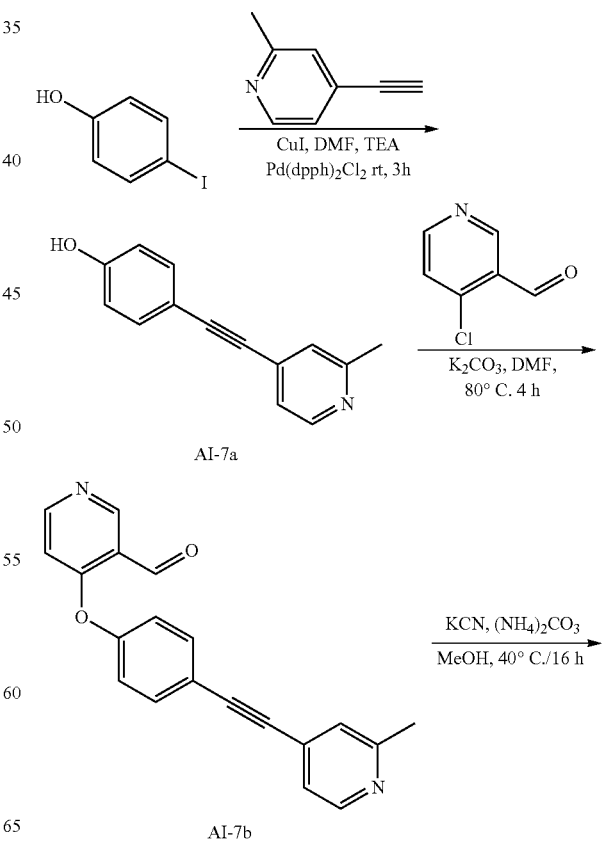

To a solution of 4-iodophenol (0.5 g, 2.27 mmol, 1.0 eq) in DMF (70 mL) was successively added 2-methyl-4-vinylpyridine (0.3 g, 2.5 mmol, 1.1 eq), PPh$_3$ (60 mg, 0.23 mmol, 0.1 eq), TEA (0.74 g, 6.81 mmol, 3 eq) and Pd(OAc)$_2$ (51 mg, 0.23 mmol, 0.1 eq) under nitrogen atmosphere. The mixture was stirred at 110° C. for 2 h. Then the reaction was

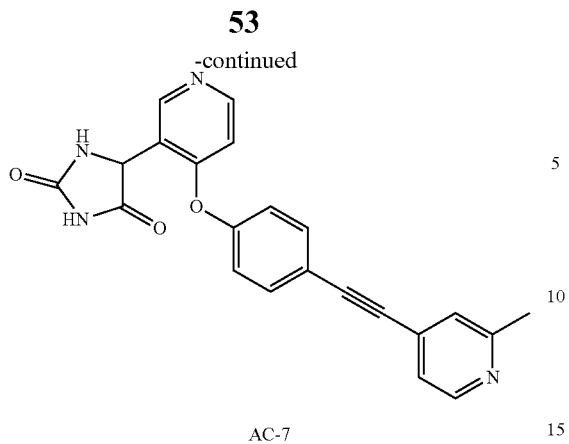

AC-7

To a solution of 4-iodophenol (2.2 g, 10 mmol, 1.0 eq) and 4-ethynyl-2-methylpyridine (1.29 g, 11 mmol, 1.1 eq) in DMF (30 mL) was added TEA (3.2 g, 30 mmol, 3 eq), Pd(Ph$_3$P)$_2$Cl$_2$ (1.4 g, 2 mmol, 0.2 eq) and CuI (0.38 g, 2 mmol, 0.2 eq) under nitrogen atmosphere. The mixture was stirred at room temperature for 3 h under nitrogen atmosphere. Then the mixture was quenched with saturated NH$_4$Cl (50 mL) solution. The mixture was extracted with ethyl acetate (30 mL*3). The combined organic phases were washed with brine, dried over anhydrous Na$_2$SO$_4$ and concentrated under reduced pressure. The residue was purified by silica gel chromatography to afford AI-7a (1.05 g, 45%).

To a solution of AI-7a (0.8 g, 3.82 mmol, 1.0 eq) in DMF (40 mL) was added 4-chloronicotinaldehyde (0.54 g, 3.82 mmol, 1.0 eq) and K$_2$CO$_3$ (1.05 g, 7.64 mmol, 2 eq). The mixture was stirred at 80° C. for 4 h. Then the mixture was diluted with water (100 mL) and extracted with ethyl acetate (50 mL*3). The organic layer was washed with brine, dried over anhydrous Na$_2$SO$_4$ and concentrated under reduced pressure. The residue was purified by silica gel chromatography to afford AI-7b (0.45 g, 37%).

To a solution of AI-7b (520 mg, 1.65 mmol, 1.0 eq) in MeOH (15 mL) was added (NH$_4$)$_2$CO$_3$ (635 mg, 6.6 mmol, 4.0 eq) and KCN (215 mg, 3.3 mmol, 2.0 eq). The mixture was stirred at 45° C. for 16 h. The reaction was added with 3 M HCl to adjust pH=1-2 and stirred at room temperature for 1 h. Then a saturated aqueous solution of NaHCO$_3$ was added to adjust pH=7-8 and the reaction was extracted with ethyl acetate. The organic layer was washed with brine, dried over anhydrous Na$_2$SO$_4$ and concentrated under reduced pressure. The residue was purified by silica gel chromatography to give AC-7 (370 mg, 58%) as a white solid.

Example 8: Preparation of Compound AC-8

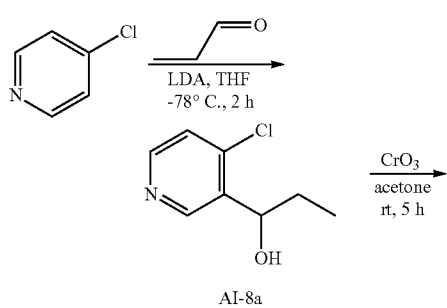

AI-8a

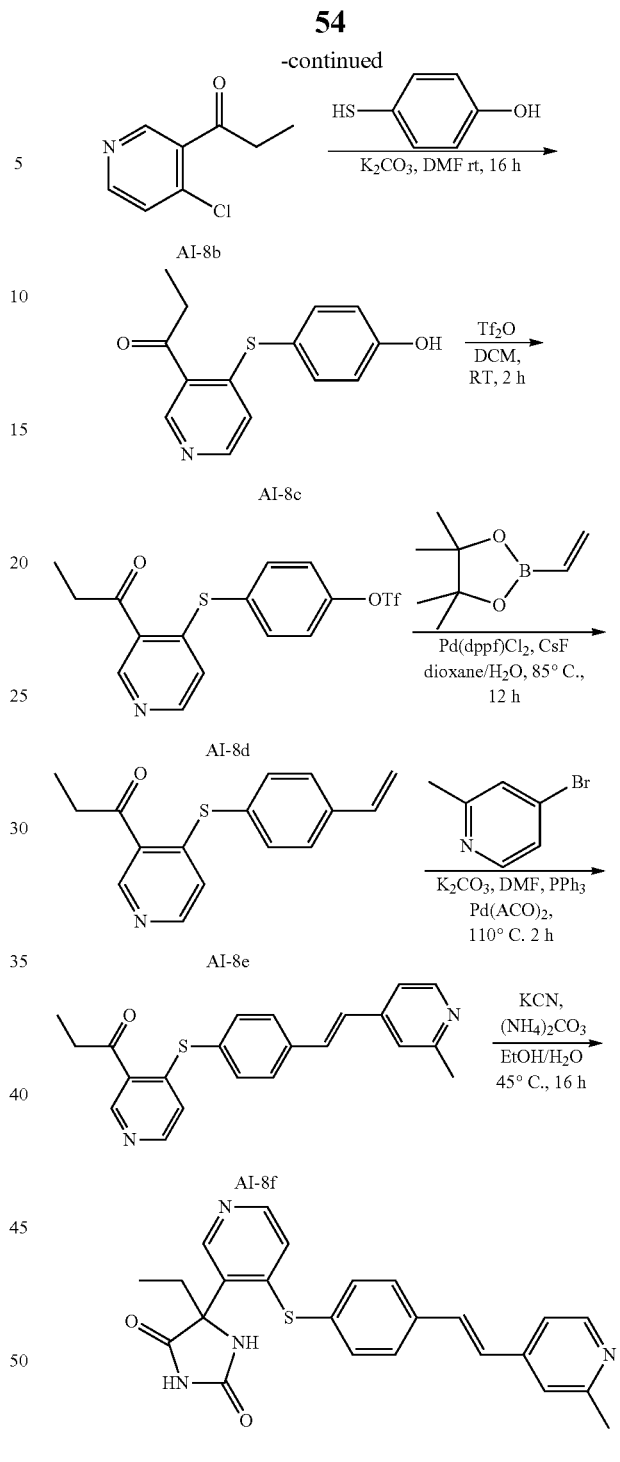

To a mixture of 4-chloropyridine (100 g, 0.667 mol, 1.0 eq) in dry THF (1 L) was quickly added LDA (2 M in THF, 733.26 mL, 1.467 mol, 2.2 eq) at −78° C. under nitrogen atmosphere. The mixture was stirred at −78° C. for 1 h. Then propionaldehyde (74.1 g, 0.999 mol, 1.5 eq) was added dropwise and the mixture was stirred for 1 h. TLC analysis of the reaction mixture showed full conversion to the desired product. The reaction was quenched with a saturated aqueous solution of NH$_4$Cl and extracted with ethyl acetate (EA) (3×500 mL). The organic layer was washed with brine and water, dried over Na$_2$SO$_4$ and concentrated in vacuum. The residue was purified by column chromatography on a silica gel (PE:EA, 3:1) to give AI-8a (45 g, 48%).

To a mixture of AI-8a (26.3 g, 0.154 mol, 1.0 eq) in acetone (300 mL) was added $CrO_3$ (30.8 g, 0.308 mol, 2.0 eq). The mixture was stirred at room temperature for 5 h. Then the mixture was filtered and the filtrate was concentrated under reduced pressure. The residue was purified by silica gel chromatography to afford AI-8b (16.0 g, 62%)

To a mixture of AI-8b (1 g, 4.67 mmol, 1.0 eq) and 4-mercaptophenol (590 mg, 4.67 mmol, 1.0 eq) in DMF (50 mL) was added $K_2CO_3$ (1.29 g, 9.34 mmol, 2 eq). The mixture was stirred at room temperature for 16 h under nitrogen atmosphere. Then the mixture was quenched with $H_2O$ (100 mL) and extracted with ethyl acetate (50 mL*3). The combined organic phases were washed with brine, dried over anhydrous $Na_2SO_4$ and concentrated under reduced pressure. The residue was purified by silica gel chromatography to afford AI-8c (1.2 g, 99%).

To a solution of AI-8c (2.37 g, 6.5 mmol, 1.0 eq) in DCM (50 mL) was added TEA (2.05 g, 19.5 mmol, 3 eq) and $(CF_3SO_2)_2O$ (2.01 g, 7.15 mmol, 1.1 eq) at −78° C. under nitrogen atmosphere. The mixture was stirred at −78° C. for 2 h under nitrogen atmosphere. Then the mixture was warmed to 0° C. and quenched with saturated $Na_2CO_3$ (20 mL) solution. The organic phases were washed with brine, dried over anhydrous $Na_2SO_4$ and concentrated under reduced pressure. The residue was purified by silica gel chromatography to afford AI-8d (2.1 g, 82%).

To a solution of AI-8d (2.1 g, 5.36 mmol, 1.0 eq) in dioxane/$H_2O$ (5/1, 60 mL) was successively added 4,4,5,5-tetramethyl-2-vinyl-1,3,2-dioxaborolane (0.9 g, 5.9 mmol, 1.1 eq), $Pd(dppf)_2Cl_2$ (0.05 g, 0.53 mmol, 0.1 eq) and CsF (2.07 g, 10.72 mmol, 2 eq) under nitrogen atmosphere. The mixture was stirred at 85° C. for 12 h. Then the reaction was cooled to room temperature and quenched with $H_2O$ (50 mL) and extracted with ethyl acetate (30 mL*3). The combined organic phases were washed with brine, dried over anhydrous $Na_2SO_4$ and concentrated under reduced pressure. The residue was purified by silica gel chromatography to afford AI-8e (1.36 g, 94%).

To a solution of AI-8e (0.6 g, 2.27 mmol, 1.0 eq) in DMF (70 mL) was successively added 4-bromo-2-methylpyridine (0.3 g, 2.5 mmol, 1.1 eq), $PPh_3$ (60 mg, 0.23 mmol, 0.1 eq), TEA (0.74 g, 6.81 mmol, 3 eq) and $Pd(OAc)_2$ (51 mg, 0.23 mmol, 0.1 eq) under nitrogen atmosphere. The mixture was stirred at 110° C. for 2 h. Then the reaction was cooled to room temperature and quenched with saturated $NH_4Cl$ solution. The mixture was extracted with ethyl acetate. The combined organic phases were washed with brine, dried over anhydrous $Na_2SO_4$ and concentrated under reduced pressure. The residue was purified by silica gel chromatography to afford AI-8f (0.3 g, 64%).

To a solution of AI-8f (300 mg, 0.83 mmol, 1.0 eq) in MeOH/$H_2O$ (12 mL, 5/1) was added $(NH_4)_2CO_3$ (320 mg, 3.32 mmol, 4.0 eq) and KCN (106 mg, 1.68 mmol, 2.0 eq). The mixture was stirred at 45° C. for 16 h. The reaction was added with 3 M HCl to adjust pH=1-2 and stirred at room temperature for 1 h. Then a saturated aqueous solution of $NaHCO_3$ was added to adjust pH=7-8 and the reaction was extracted with ethyl acetate. The organic layer was washed with brine, dried over anhydrous $Na_2SO_4$ and concentrated under reduced pressure. The residue was purified by Prep-HPLC to give AC-8 (29.5 mg, 8%).

Example 9: Preparation of Compound AC-9

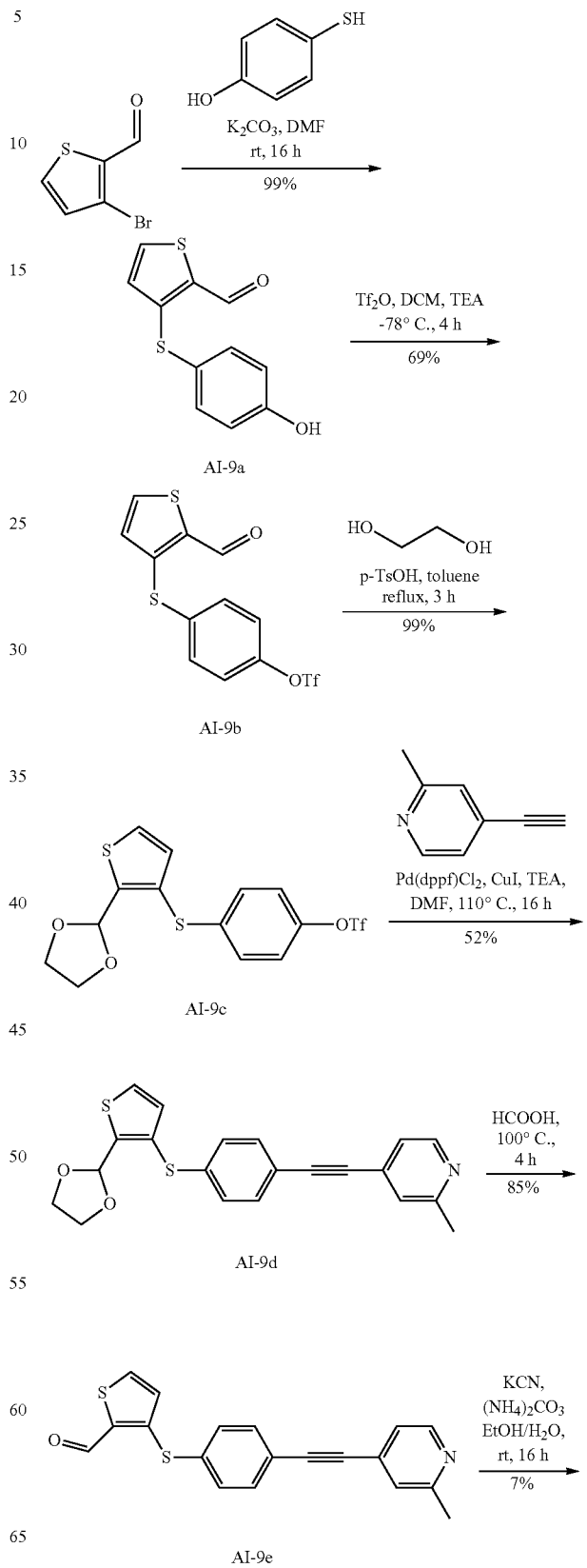

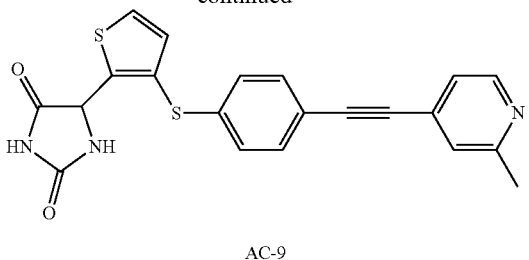

AC-9

To a solution of compound AI-9e (2.93 g, 8.7 mmol, 1.0 eq) in EtOH/H₂O (30 mL/30 mL) was added (NH₄)₂CO₃ (3.39 g, 34.9 mmol, 4.0 eq) and KCN (1.0 g, 17.4 mmol, 2.0 eq). The reaction mixture was stirred at room temperature for 16 h. The mixture was diluted with H₂O (100 mL), extracted with EA (50 mL×3). The combined organic layers were washed with brine, dried over Na₂SO₄ and concentrated. The residue was purified by column chromatography on a silica gel (DCM:EA=1:1) to afford compound AC-9 (278 mg, 7%) as a yellow solid.

Example 10: Preparation of Compound AC-10

To a solution of 3-bromothiophene-2-carbaldehyde (10.0 g, 52.3 mol, 1.0 eq) in DMF (100 mL) was added 4-mercaptophenol (7.93 g, 62.8 mol, 1.2 eq) and K₂CO₃ (21.04 g, 157.0 mol, 3.0 eq) at rt under nitrogen atmosphere. The mixture was stirred at rt for 16 h. The reaction was quenched with ice water (300 mL) and extracted with EA (3×100 mL). The combined organic layers were washed with brine, dried over Na₂SO₄ and concentrated in vacuum. The residue was purified by column chromatography on a silica gel (PE/EA: 1/1) to give compound AI-9a (12.3 g, 99%).

To a solution of compound AI-9a (7.6 g, 32.2 mmol, 1.0 eq) in DCM (150 mL) was added Tf₂O (13.6 g, 48.24 mmol, 1.5 eq) and DIEA (12.47 g, 96.6 mol, 3.0 eq) at 78° C. under nitrogen atmosphere. The mixture was stirred at −78° C. for 4 h. Then the reaction was filtered and quenched with ice water (200 mL). The mixture was extracted with ethyl acetate (50 mL×3). The combined organic layers were washed with brine, dried over anhydrous Na₂SO₄ and concentrated under reduced pressure. The residue was purified by column chromatography on silica gel (PE/EA: 1/1) to afford compound AI-9b (8.2 g, 69%).

To a solution of compound AI-9b (10.0 g, 27.1 mmol, 1.0 eq) in toluene (150 mL) was added ethane-1,2-diol (16.85 g, 271.5 mmol, 10.0 eq) and TsOH (0.51 g, 2.7 mol, 0.1 eq) at rt. The mixture was stirred under reflux for 4 h. Then the reaction was cooled to room temperature and quenched with ice water (200 mL). The solution was extracted with ethyl acetate (100 mL×2). The combined organic layers were dried over anhydrous Na₂SO₄ and concentrated under reduced pressure. The residue was purified by column chromatography on a silica gel (DCM/EA: 1/1) to afford compound AI-9c (11.1 g, 99%)

To a mixture of compound AI-9c (6.0 g, 14.5 mmol, 1.0 eq), 4-ethynyl-2-methylpyridine (1.87 g, 15.9 mmol, 1.1 eq), CuI (0.26 g, 1.4 mmol, 0.1 eq) and TEA (4.39 g, 43.5 mol, 3 eq) in DMF (70 mL) was added Pd(dppf)Cl₂ (1.02 g, 1.4 mmol, 0.1 eq) under nitrogen atmosphere. The mixture was stirred at 110° C. for 16 h. Then the reaction was cooled to room temperature and quenched with ice water (200 mL). The solution was extracted with ethyl acetate (100 mL×3). The combined organic layers were dried over anhydrous Na₂SO₄ and concentrated under reduced pressure. The residue was purified by column chromatography on a silica gel (DCM/EA: 1/1) to afford compound AI-9d (2.9 g, 52%)

A solution of compound AI-9d (3.88 g, 10.2 mmol, 1.0 eq) in HCOOH (40 mL) was stirred at 100° C. for 4 h. The mixture was concentrated under reduced pressure. The residue was diluted with saturated NaHCO₃ aqueous (100 mL), extracted with EA (50 mL×3). The combined organic layers were washed with brine, dried over Na₂SO₄ and concentrated. The residue was purified by column chromatography on a silica gel (DCM:EA=1:1) to afford compound AI-9e (2.93 g, 85%)

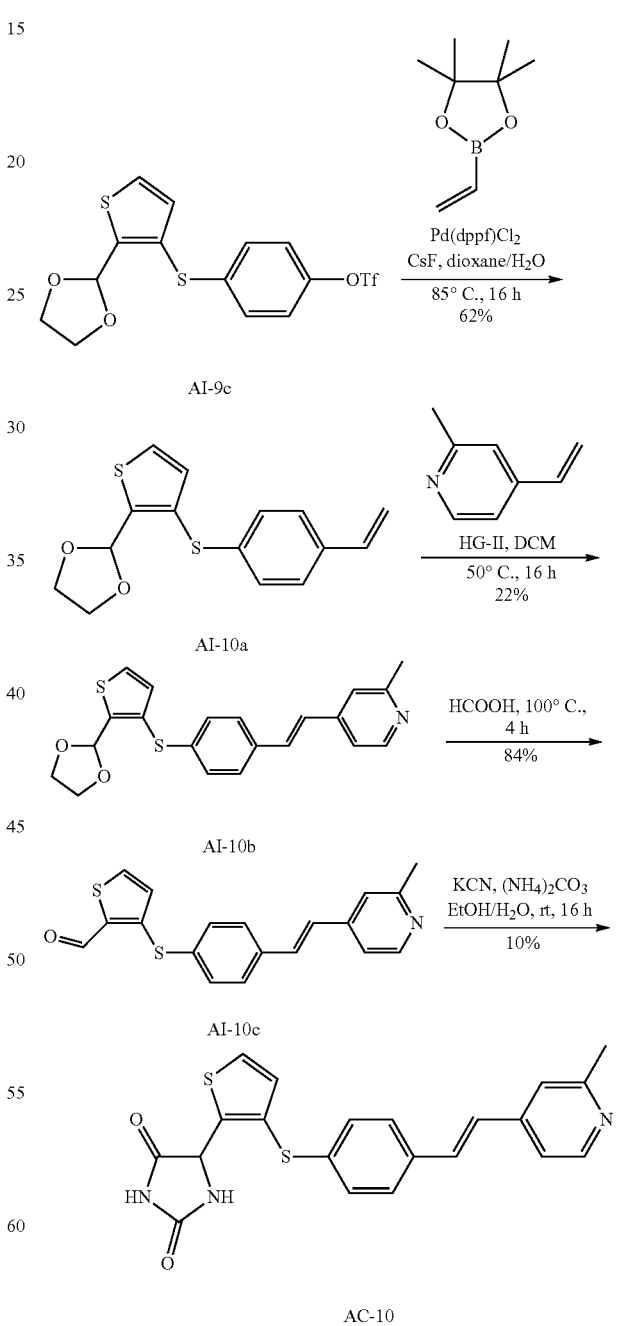

AI-9c

AI-10a

AI-10b

AI-10c

AC-10

To a mixture of compound AI-9c (5.1 g, 12.4 mmol, 1.0 eq), 4,4,5,5-tetramethyl-2-vinyl-1,3,2-dioxaborolane (3.82 g, 24.8 mmol, 2.0 eq), CsF (4.15 g, 24.8 mmol, 2.0 eq) in dioxane/H$_2$O (90 mL/10 mL) was added Pd(dppf)Cl$_2$ (0.91 g, 1.2 mmol, 0.1 eq) under nitrogen atmosphere. The mixture was stirred at 85° C. for 16 h. Then the reaction was cooled to room temperature and quenched with ice water (200 mL). The solution was extracted with ethyl acetate (50 mL×3). The combined organic layers were dried over anhydrous Na$_2$SO$_4$ and concentrated under reduced pressure. The residue was purified by column chromatography on a silica gel (PE/EA: 1/1) to afford compound AI-10a (2.24 g, 62%)

To a mixture of compound AI-10a (1.15 g, 4.0 mmol, 1.0 eq), 2-methyl-4-vinylpyridine (0.48 g, 4.0 mmol, 1.0 eq) in DCM (100 mL) was added Hoveyda-Grubbs II (0.25 g, 0.4 mmol, 0.1 eq) under nitrogen atmosphere. The mixture was stirred at 50° C. for 16 h. Then the reaction was cooled to room temperature and quenched with ice water (100 mL). The solution was extracted with ethyl acetate (50 mL×3). The combined organic layers were dried over anhydrous Na$_2$SO$_4$ and concentrated under reduced pressure. The residue was purified by column chromatography on a silica gel (DCM/EA: 1/1) to afford compound AI-10b (0.34 g, 22%)

A solution of compound AI-10b (1.34 g, 3.5 mmol, 1.0 eq) in HCOOH (30 mL) was stirred at 100° C. for 4 h. The mixture was concentrated under reduced pressure. The residue was diluted with saturated NaHCO$_3$ aqueous (100 mL) and extracted with EA (50 mL×3). The combined organic layers were washed with brine, dried over Na$_2$SO$_4$ and concentrated. The residue was purified by column chromatography on a silica gel (DCM:EA=1:1) to afford compound AI-10c (1.0 g, 84%)

To a solution of compound AI-10c (1.2 g, 3.6 mmol, 1.0 eq) in EtOH/H$_2$O (15 mL/15 mL) was added (NH$_4$)$_2$CO$_3$ (1.38 g, 14.2 mmol, 4.0 eq) and KCN (0.41 g, 7.2 mmol, 2.0 eq). The reaction mixture was stirred at room temperature for 16 h. The mixture was diluted with H$_2$O (50 mL), extracted with EA (50 mL×3). The combined organic layers were washed with brine, dried over Na$_2$SO$_4$ and concentrated. The residue was purified by column chromatography on a silica gel (DCM:EA=1:1) to afford compound AC-10 (147 mg, 10%) as a yellow solid.

Example 11: Preparation of Compound AC-11

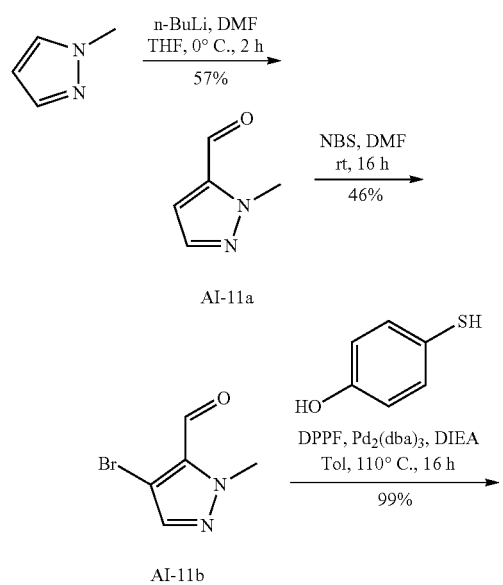

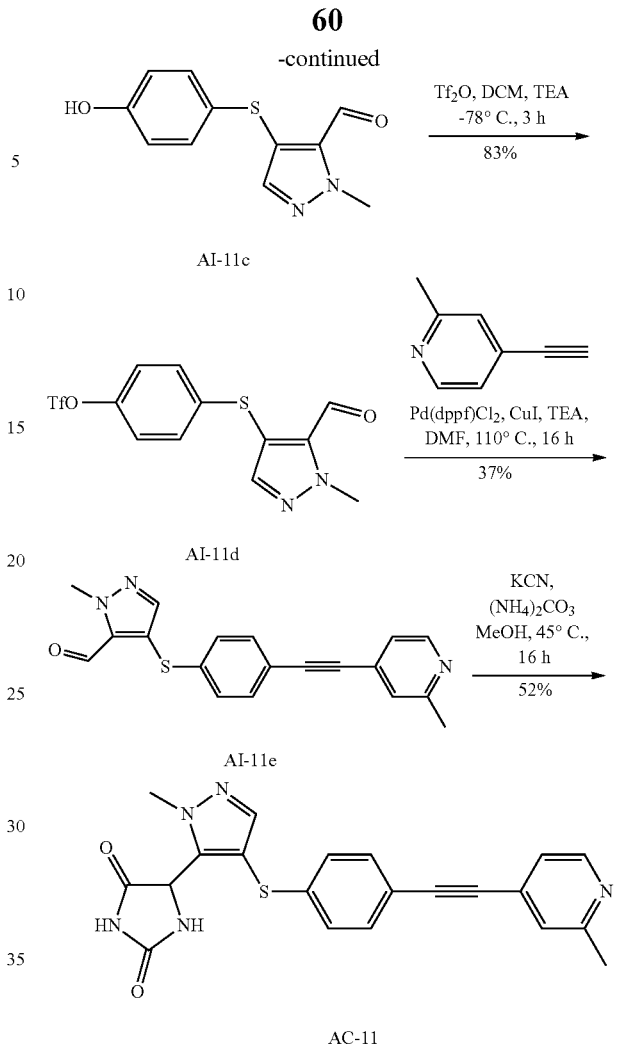

To a solution of 1-methyl-1H-pyrazole (10.0 g, 0.12 mol, 1.0 eq) in dry THF (100 mL) was added n-BuLi (2.5 M in hexane, 58 mL, 0.15 mol, 1.2 eq) at −78° C. under nitrogen atmosphere. The mixture was stirred at −78° C. for 1 h. Then DMF (18.5 mL, 0.24 mol, 2.0 eq) was added dropwise and the mixture was stirred for 1 h. TLC analysis of the reaction mixture showed full conversion to the desired product. The reaction was quenched with saturated aqueous of NH$_4$Cl and extracted with EA (3×500 mL). The combined organic layers were washed with brine, dried over Na$_2$SO$_4$ and concentrated in vacuum. The residue was purified by column chromatography on a silica gel (PE/EA: 1/1) to give compound AI-11a (7.7 g, 57%).

To a solution of AI-11a (8.0 g, 72.65 mmol, 1.0 eq) in DMF (80 mL) was added NBS (12.86 g, 108.98 mmol, 1.5 eq). The mixture was stirred at room temperature for 16 h under nitrogen atmosphere. Then the mixture was filtered and quenched with ice water (200 mL). The mixture was extracted with ethyl acetate (100 mL×3). The combined organic layers were dried over anhydrous Na$_2$SO$_4$ and concentrated under reduced pressure. The residue was purified by column chromatography on silica gel (PE/EA: 1/1) to afford compound AI-11b (6.4 g, 46%).

To a mixture of compound AI-11b (5.7 g, 30.16 mmol, 1.0 eq), 4-mercaptophenol (4.19 g, 33.17 mmol, 1.1 eq), DPPF (0.25 g, 3.02 mmol, 0.1 eq) and DIEA (5.84 g, 45.24 mol, 1.5 eq) in toluene (60 mL) was added Pd$_2$(dba)$_3$ (1.22 g, 2.11 mmol, 0.07 eq) under nitrogen atmosphere. The mixture was stirred at 110° C. for 16 h. Then the reaction was filtered and quenched with ice water (100 mL). The mixture was extracted with ethyl acetate (50 mL×3). The combined organic layers were dried over anhydrous Na₂SO₄ and concentrated under reduced pressure. The residue was purified by column chromatography on a silica gel (DCM/EA: 1/1) to afford compound AI-11c (7.1 g, 99%)

To a solution of compound AI-11c (7.1 g, 30.3 mmol, 1.0 eq) in DCM (150 mL) was added Tf₂O (12.83 g, 45.46 mmol, 1.5 eq) and DIEA (11.73 g, 90.9 mol, 3.0 eq) at −78° C. under nitrogen atmosphere. The mixture was stirred at −78° C. for 3 h. Then the reaction was filtered and quenched with ice water (200 mL). The mixture was extracted with ethyl acetate (50 mL×3). The combined organic layers were washed with brine, dried over anhydrous Na₂SO₄ and concentrated under reduced pressure. The residue was purified by column chromatography on a silica gel (PE/EA: 1/1) to afford compound AI-11d (9.3 g, 83%).

To a mixture of compound AI-11d (1.1 g, 3.0 mmol, 1.0 eq), 4-ethynyl-2-methylpyridine (0.35 g, 3.0 mmol, 1.0 eq), CuI (57 mg, 0.3 mmol, 0.1 eq) and TEA (0.91 g, 9.0 mol, 3 eq) in toluene (20 mL) was added Pd(dppf)Cl₂ (0.22 g, 0.3 mmol, 0.1 eq) under nitrogen atmosphere. The mixture was stirred at 110° C. for 16 h. Then the reaction was cooled to room temperature and quenched with ice water (100 mL). The solution was extracted with ethyl acetate (50 mL×3). The combined organic layers were dried over anhydrous Na₂SO₄ and concentrated under reduced pressure. The residue was purified by column chromatography on a silica gel (DCM/EA: 1/1) to afford compound AI-11e (0.38 g, 37%)

To a solution of compound AI-11e (0.49 g, 1.47 mmol, 1.0 eq) in MeOH (10 mL) was added (NH₄)₂CO₃ (0.57 g, 5.88 mmol, 4.0 eq) and KCN (0.19 g, 2.94 mmol, 2.0 eq). The reaction mixture was stirred at 40° C. overnight under nitrogen atmosphere. The mixture was diluted with H₂O (50 mL), extracted with EA (30 mL×3). The combined organic layers were washed with brine, and dried over Na₂SO₄ and concentrated. The residue was purified by column chromatography on a silica gel (DCM:EA=1:1) to afford compound AC-11 (0.31 g, 52%) as a gray solid.

Example 12: Preparation of Compound AC-12

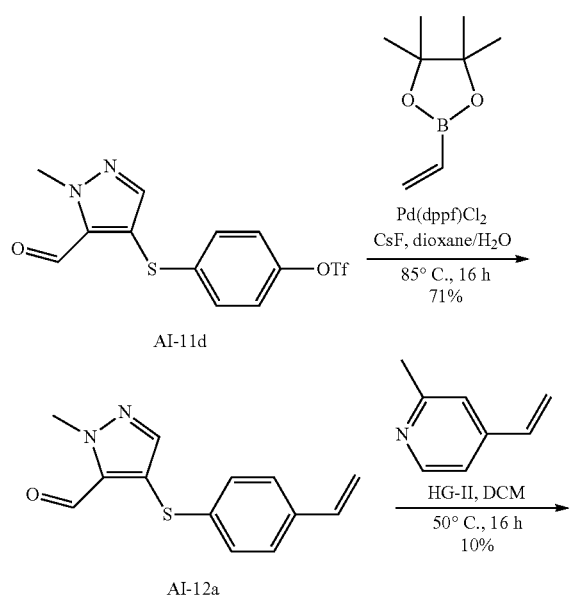

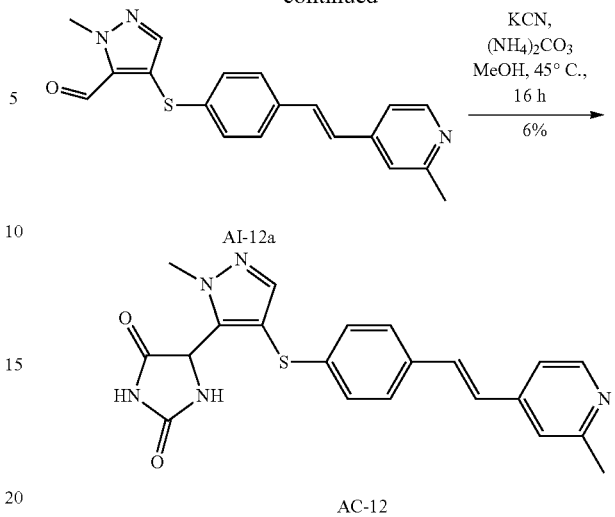

To a mixture of compound AI-11d (5.0 g, 13.65 mmol, 1.0 eq), 4,4,5,5-tetramethyl-2-vinyl-1,3,2-dioxaborolane (4.2 g, 27.3 mmol, 2.0 eq), CsF (4.15 g, 27.3 mmol, 2.0 eq) in dioxane/H₂O (90 mL/10 mL) was added Pd(dppf)Cl₂ (1.98 g, 2.7 mmol, 0.1 eq) under nitrogen atmosphere. The mixture was stirred at 85° C. for 16 h. Then the reaction was cooled to room temperature and quenched with ice water (100 mL). The solution was extracted with ethyl acetate (50 mL×3). The combined organic layers were dried over anhydrous Na₂SO₄ and concentrated under reduced pressure. The residue was purified by column chromatography on a silica gel (PE/EA: 1/1) to afford compound AI-12a (2.4 g, 71%)

To a mixture of compound AI-12a (4.8 g, 19.6 mmol, 1.0 eq), 2-methyl-4-vinylpyridine (4.68 g, 39.3 mmol, 2.0 eq) in DCM (100 mL) was added Hoveyda-Grubbs II (0.99 g, 2.0 mmol, 0.1 eq) under nitrogen atmosphere. The mixture was stirred at 50° C. for 16 h. Then the reaction was cooled to room temperature and quenched with ice water (100 mL). The solution was extracted with ethyl acetate (50 mL×3). The combined organic layers were dried over anhydrous Na₂SO₄ and concentrated under reduced pressure. The residue was purified by column chromatography on a silica gel (DCM/EA: 1/1) to afford compound AI-12b (0.7 g, 10%)

To a solution of compound AI-12b (0.7 g, 2.09 mmol, 1.0 eq) in MeOH (10 mL) was added (NH₄)₂CO₃ (0.81 g, 8.35 mmol, 4.0 eq) and KCN (0.27 g, 4.17 mmol, 2.0 eq). The reaction mixture was stirred at 40° C. overnight under nitrogen atmosphere. The mixture was diluted with H₂O (50 mL), extracted with EA (30 mL×3). The combined organic layers were washed with brine, dried over Na₂SO₄ and concentrated. The residue was purified by column chromatography on silica gel (DCM:EA=1:1) to afford compound AC-12 (51 mg, 6%) as a yellow solid.

Biological Testing

Example 1: MMP Inhibitory Assays

The inhibitory effect of compounds on the rate of cleaving fluorogenic MMP substrate (Enzo, BML-P128) by recombinant human MMP-12 catalytic domain (Enzo, BML-SE138) was carried out by methods known in the art. Briefly, to each well of a 96-well black opaque plate, all the reagents were sequentially added by pipetting, and the final reaction contained 4 nM of recombinant human MMP-12 catalytic domain, 4 μM of fluorogenic MMP substrate, and various concentrations (0.057 nM to 1,000 nM) of tested compound dilutions in HEPES buffer (pH 7.5) containing 10 mM of CaCl$_2$, 0.01% Brij® 35 (polyoxyethylene (23) lauryl ether), and 0.1 mg/ml of BSA.

The enzyme and compounds were pre-incubated on a shaker to mix in wells. After an hour of mixing, fluorogenic substrate was added to each well. Reaction without enzyme was used as a blank control in the plate. The plate was then fed into a plate reader to measure fluorescence intensity at Excitation/Emission wavelengths of 340 nm/440 nm every 10 mins for at least 1 hour at 37° C. The IC$_{50}$ of each compound in MMP-12 inhibition was determined by using a readout obtained at time point 30 minutes. The results for each compound tested are show in Table 1.

Example 2: Selectivity Assay

The MMP selectivity assay was performed by using other recombinant human MMPs, including MMP-1, MMP-2, MMP-3, MMP-7, MMP-8, MMP-9, MMP-10, MMP-12, MMP-13, and MMP-14. The IC$_{50}$ of the compounds for the other recombinant human MMPs was determined as described above in Example 1, and are shown in Table 2. The IC$_{50}$ values are reported as follows: A=less than 1 nM, B=1 nM to 10 nM, C=10 nM to 100 nM, D=greater than 100 nM.

TABLE 2

Selectivity Profile of Some Compounds

| Target: | AC-01 | AC-02 | AC-03 | AC-04 | AC-05 | AC-06 | AC-07 | AC-09 | AC-10 | AC-11 | AC-12 |
|---|---|---|---|---|---|---|---|---|---|---|---|
| MMP 1 | D | D | D | D | D | D | D | D | D | D | D |
| MMP 2 | D | B | B | D | C | C | D | C | B | C | B |
| MMP 3 | D | C | C | D | D | D | D | D | C | D | D |
| MMP 7 | D | D | D | D | D | D | D | D | D | D | D |
| MMP 8 | D | C | B | D | D | C | D | C | B | C | C |
| MMP 9 | D | C | C | D | D | D | D | D | C | D | D |
| MMP 10 | D | D | C | D | D | D | D | D | D | D | D |
| MMP 12 | C | A | A | B | A | A | B | A | A | A | A |
| MMP 13 | D | C | C | D | D | D | D | D | B | D | C |
| MMP 14 | D | D | D | D | D | D | D | D | D | D | D |

REFERENCES

1. U.S. Pat. No. 7,179,831
2. WO 02/096426
3. US 2004/0067996
4. WO 2004/108086
5. WO 02/074752
6. WO 2004/020415
7. US 20190352287
8. US 20190352288
9. EP1676846
10. WO/2008/065393
11. U.S. Pat. No. 7,700,604

We claim:

1. A compound of formula (I):

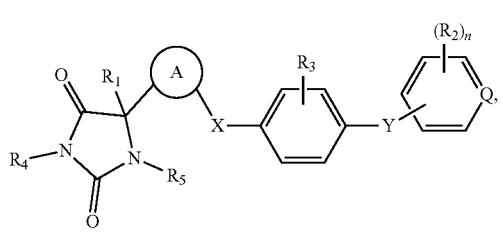

or a tautomer, stereoisomer, pharmaceutically acceptable salt, or hydrate thereof, wherein:

ring A is an optionally substituted heteroaryl;
Q is CR$_2$ or N;
R$_1$ is hydrogen or alkyl;
each R$_2$ is independently hydrogen, alkyl, halo, hydroxyl, haloalkyl, alkoxy, alkylthio, amino, amido, alkylamino, aminoalkyl, cyano, hydroxyalkyl, —(CH$_2$)$_p$C(O)OR$_6$, or —(CH$_2$)$_p$OC(O)R$_6$;
R$_3$ is hydrogen, halo, or alkyl;
each R$_4$ and R$_5$ is independently hydrogen or alkyl;
each R$_6$ is independently hydrogen or alkyl, wherein the alkyl is unsubstituted or substituted with one or more groups independently selected from amino, hydroxyl, halo, and alkoxy;
X is S or O;
Y is:

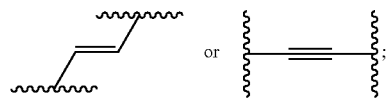

n is 1, 2, 3 or 4; and
p is 0, 1, 2, 3, 4, or 5.

2. The compound of claim 1, wherein ring A is a 5- to 6-membered monocyclic heteroaryl having 1 to 3 heteroatoms independently selected from O, S and N, wherein the 5- to 6-membered monocyclic heteroaryl is optionally substituted with alkyl.

3. The compound of claim 1, wherein ring A is pyridinyl, furanyl, thienyl, or N-methyl pyrazolyl.

4. The compound of claim 1, wherein ring A is:

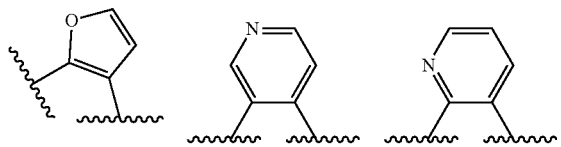

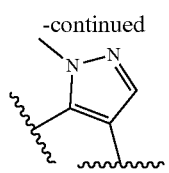

5. The compound of claim 1, wherein $R_1$ is hydrogen or $C_{1-4}$ alkyl.

6. The compound of claim 1, wherein n is 1 and $R_2$ is —$CH_3$.

7. The compound of claim 1, wherein $R_3$ is hydrogen.

8. The compound of claim 1, wherein each of $R_4$ and $R_5$ is hydrogen.

9. The compound of claim 1, wherein X is S.

10. The compound of claim 1, wherein X is O.

11. The compound of claim 1, wherein Q is N.

12. The compound of claim 1, wherein Y is:

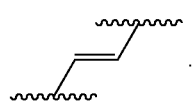

13. The compound of claim 1, wherein Y is:

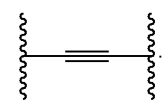

14. The compound of claim 1, wherein:

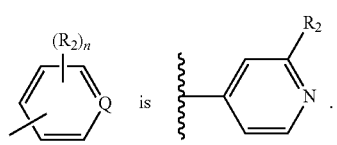

15. The compound of claim 1, wherein:
ring A is pyridinyl, furanyl, thienyl, or N-methyl pyrazolyl;
$R_1$ is hydrogen, —$CH_3$ or —$CH_2CH_3$;
$R_2$ is —$CH_3$, —C(O)$NH_2$, —$CH_2OH$, —$OCH_3$, or —OH;
each of $R_3$, $R_4$, and $R_5$ is hydrogen;
X is S or O;

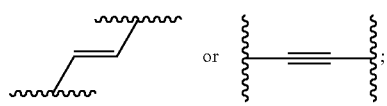

Y is
Q is CH or N; and
n is 1.

16. A compound selected from the group consisting of:

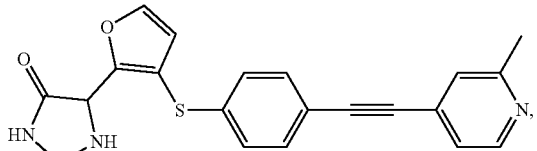

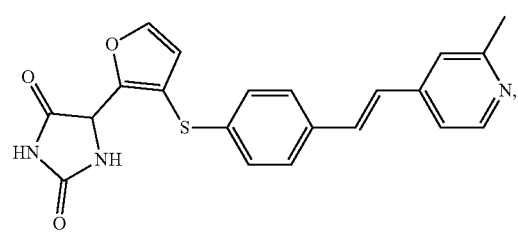

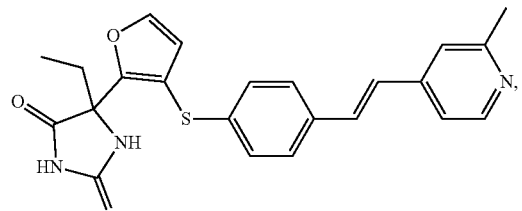

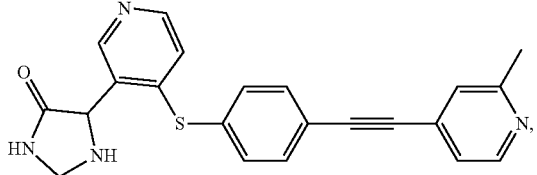

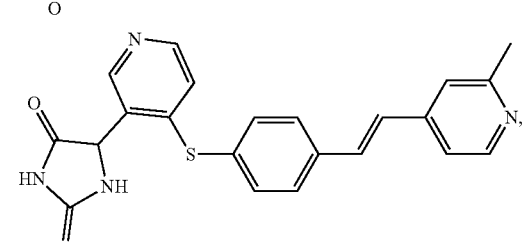

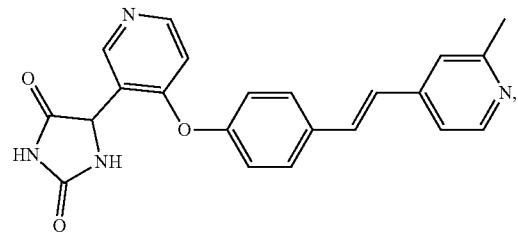

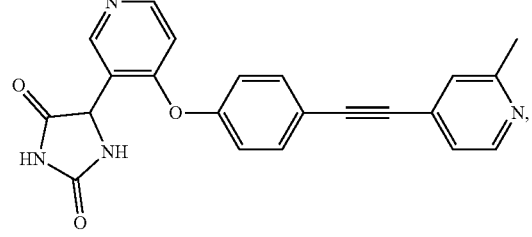

-continued

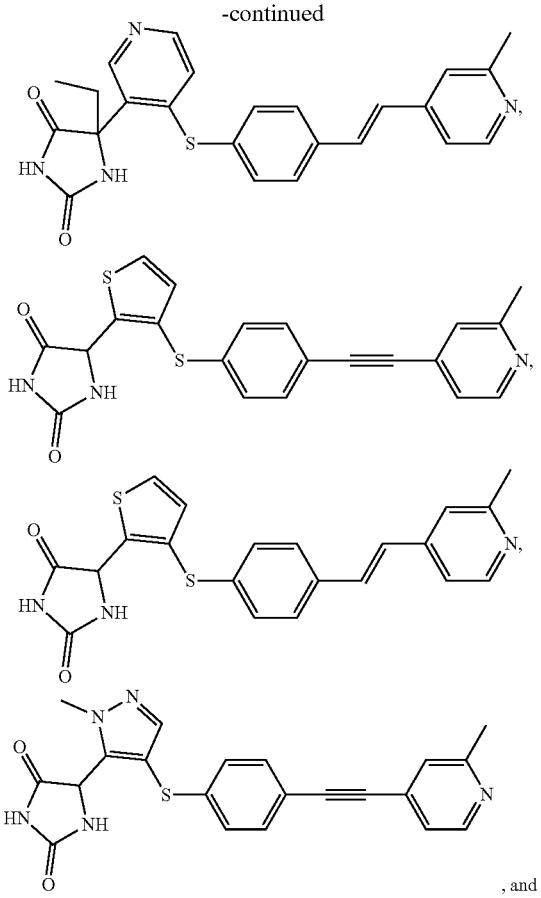

, and

-continued

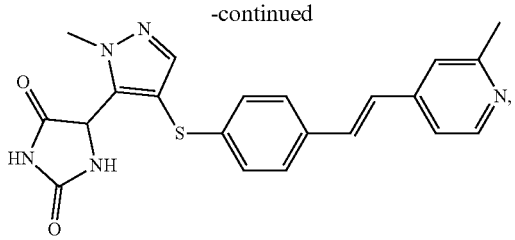

or a tautomer, stereoisomer, pharmaceutically acceptable salt, or hydrate thereof.

17. The compound of claim 16, or a pharmaceutically acceptable salt thereof.

18. A pharmaceutical composition comprising the compound of claim 1, and at least one pharmaceutically acceptable carrier.

19. A method of inhibiting macrophage elastase (MMP-12) in a subject in need thereof, the method comprising administering to the subject the pharmaceutical composition of claim 18.

20. A method of treating a disease mediated by macrophage elastase (MMP-12) in a subject in need thereof, the method comprising administering to the subject the pharmaceutical composition of claim 18, wherein the disease is selected from the group consisting of asthma, chronic obstructive pulmonary disease (COPD), a emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

* * * * *

UNITED STATES PATENT AND TRADEMARK OFFICE
CERTIFICATE OF CORRECTION

| | |
|---|---|
| PATENT NO. | : 11,673,884 B2 |
| APPLICATION NO. | : 17/097314 |
| DATED | : June 13, 2023 |
| INVENTOR(S) | : Wenjin Yang et al. |

Page 1 of 1

It is certified that error appears in the above-identified patent and that said Letters Patent is hereby corrected as shown below:

In the Claims

Claim 20, Column 68, Lines 27-34:
"the group consisting of asthma, chronic obstructive pulmonary disease (COPD), a emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis."

Should be replaced with:
--the group consisting of asthma and chronic obstructive pulmonary disease (COPD).--

Signed and Sealed this
Eleventh Day of November, 2025

John A. Squires
*Director of the United States Patent and Trademark Office*